US00RE49580E

(19) United States
(12) Reissued Patent
Kreitenberg

(10) Patent Number: US RE49,580 E
(45) Date of Reissued Patent: Jul. 18, 2023

(54) SANITIZING SURFACES

(71) Applicant: DIMER, LLC, Los Angeles, CA (US)

(72) Inventor: Arthur Kreitenberg, Los Angeles, CA (US)

(73) Assignee: DIMER, LLC, Los Angeles, CA (US)

(21) Appl. No.: 16/993,123

(22) Filed: Aug. 13, 2020

Related U.S. Patent Documents

Reissue of:
(64) Patent No.: 10,159,761
Issued: Dec. 25, 2018
Appl. No.: 15/008,191
Filed: Jan. 27, 2016

U.S. Applications:
(63) Continuation-in-part of application No. 14/679,890, filed on Apr. 6, 2015, now Pat. No. 10,406,253, and a continuation-in-part of application No. 14/679,914, filed on Apr. 6, 2015, now Pat. No. 9,149,549, and a continuation-in-part of application No. 14/679,860,
(Continued)

(51) Int. Cl.
*A61L 2/10* (2006.01)
*B64F 5/30* (2017.01)

(52) U.S. Cl.
CPC *A61L 2/10* (2013.01); *B64F 5/30* (2017.01); *A61L 2202/16* (2013.01); *A61L 2202/25* (2013.01)

(58) Field of Classification Search
CPC .... A61L 2/10; A61L 2202/16; A61L 2202/25; B64F 5/30
See application file for complete search history.

(56) References Cited

U.S. PATENT DOCUMENTS 2,273,449 A * 2/1942 Plishker ..... A47K 13/302 250/455.11
5,338,169 A 8/1994 Buckley
(Continued)

FOREIGN PATENT DOCUMENTS

CN 2621044 Y * 6/2004
CN 101756678 6/2010
(Continued)

OTHER PUBLICATIONS

Universal Joint, Wikipedia [retrieved on Mar. 24, 2022], Retrieved from the Internet: <URL: https://en.wikipedia.org/wiki/Universal_joint>. (Year: 2022).*
(Continued)

*Primary Examiner* — Elizabeth L McKane
(74) *Attorney, Agent, or Firm* — Greenberg Traurig, LLP

(57) ABSTRACT

Sanitizing surfaces in a location related to aircraft. There are multiple rows of seats. A sanitization device includes a mobile body configured to travel along the aisle of the aircraft. An arm extends from the sanitization device laterally from the mobile body across the seats, and a source of UV radiation mounted on the sanitization device is directed across the seats exposing surfaces in the passenger area to UV radiation. There can be a unit hand operated, pushed down the aisle by hand, wings deployed and stowed by hand. There can be a plug in version with long extension cords that a human can keep from tangling. The operator can be protected with skin and eye protective gear and there can be remote control by an operator standing nearby.

37 Claims, 34 Drawing Sheets

Related U.S. Application Data filed on Apr. 6, 2015, now Pat. No. 9,144,618, and a continuation-in-part of application No. 14/533,814, filed on Nov. 5, 2014, now Pat. No. 8,999,238, which is a continuation of application No. 13/779,635, filed on Feb. 27, 2013, now Pat. No. 8,907,304.

(56) References Cited

U.S. PATENT DOCUMENTS

| | | | | |
|---|---|---|---|---|
| 5,369,892 | A | 12/1994 | Dhaemers | |
| 5,673,918 | A | 10/1997 | Bigari | |
| 5,959,423 | A | 9/1999 | Nakanishi et al. | |
| 6,311,974 | B1 | 11/2001 | Koga | |
| 6,370,453 | B2 | 4/2002 | Sommer | |
| 6,389,639 | B1 | 5/2002 | Worsham | |
| 6,419,190 | B1 | 7/2002 | Nguegang | |
| 6,565,668 | B1 | 5/2003 | Sandberg et al. | |
| 6,779,714 | B2 | 8/2004 | Webb | |
| 6,787,782 | B1 | 9/2004 | Krosney et al. | |
| 6,889,449 | B2 | 5/2005 | Silver | |
| 6,992,301 | B2 | 1/2006 | Fenc | |
| 7,204,208 | B2 | 4/2007 | Johnson et al. | |
| 7,459,694 | B2 | 12/2008 | Scheir et al. | |
| 7,459,695 | B2 | 12/2008 | Hanley et al. | |
| 7,462,849 | B2 | 12/2008 | Ferres et al. | |
| 7,523,692 | B1 | 4/2009 | Burns | |
| 8,029,739 | B2 | 10/2011 | Field et al. | |
| 8,105,532 | B2 | 1/2012 | Harmon et al. | |
| 8,193,515 | B2 | 6/2012 | Kreitenberg | |
| 8,226,887 | B2 | 7/2012 | Harmon et al. | |
| 8,330,121 | B2 | 12/2012 | Douglas | |
| 8,999,238 | B2 * | 4/2015 | Kreitenberg | B64D 11/0007 422/24 |
| 9,144,618 | B2 | 9/2015 | Kreitenberg | |
| 9,149,549 | B2 * | 10/2015 | Kreitenberg | B64D 11/0007 |
| 10,195,298 | B2 | 2/2019 | Kreitenberg | |
| 2004/0056201 | A1 | 3/2004 | Fink et al. | |
| 2004/0244138 | A1 | 12/2004 | Taylor et al. | |
| 2005/0022844 | A1 | 2/2005 | Field et al. | |
| 2005/0159275 | A1 | 7/2005 | Bullman et al. | |
| 2006/0216193 | A1 | 9/2006 | Johnson et al. | |
| 2007/0158499 | A1 | 7/2007 | Whittingham | |
| 2008/0056933 | A1 | 3/2008 | Moore et al. | |
| 2008/0184518 | A1 | 8/2008 | Taylor et al. | |
| 2009/0193676 | A1 | 8/2009 | Shengguang et al. | |
| 2010/0028201 | A1 | 2/2010 | Neister | |
| 2011/0082668 | A1 | 4/2011 | Escrig et al. | |
| 2011/0167574 | A1 | 7/2011 | Stout et al. | |
| 2011/0214686 | A1 * | 9/2011 | Chavana, Jr. | A47L 9/00 134/1 |
| 2012/0221192 | A1 | 8/2012 | Seibt | |
| 2012/0223216 | A1 | 9/2012 | Flaherty et al. | |
| 2013/0000675 | A1 | 1/2013 | Hong et al. | |
| 2013/0270459 | A1 | 10/2013 | Fontani | |
| 2014/0044590 | A1 | 2/2014 | Trapani | |
| 2014/0241941 | A1 * | 8/2014 | Kreitenberg | A61L 2/10 422/24 |
| 2015/0064065 | A1 * | 3/2015 | Kreitenberg | A61L 2/10 422/24 |
| 2015/0209459 | A1 | 7/2015 | Kreitenberg | |
| 2017/0326262 | A1 | 11/2017 | Paver, Jr. | |
| 2018/0256764 | A1 | 9/2018 | Kreitenberg | |

FOREIGN PATENT DOCUMENTS

| | | | |
|---|---|---|---|
| CN | 202314543 U | * | 7/2012 |
| CN | 202554525 U | * | 11/2012 |
| DE | 3937706 | | 5/1991 |
| GB | 2391799 | | 2/2004 |
| JP | S63-135646 U | | 9/1988 |
| JP | H10-57614 | | 3/1998 |
| JP | 2000-325059 | | 11/2000 |
| JP | 2005-013723 | | 1/2005 |
| JP | 2007-082747 | | 4/2007 |
| JP | 2009-291349 | | 12/2009 |
| JP | 2011-098156 | | 5/2011 |
| WO | WO2008/010684 | | 1/2008 |
| WO | WO 2008/010684 A1 | | 1/2008 |
| WO | WO2014/036217 | | 3/2014 |
| WO | WO 2014/036217 A1 | | 3/2014 |

OTHER PUBLICATIONS

International Search Report and Written Opinion, dated Jul. 13, 2016, from related International Patent App. No. PCT/US2016/026048.

European Search Report for European Patent Application No. EP14155515, completed on May 23, 2014 in Munich.

* cited by examiner

SANITIZING SURFACES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION

This application is a continuation-in-part of U.S. Utility patent application Ser. No. 14/679,890, filed Apr. 6, 2015, currently pending. This application is also a continuation-in-part of U.S. Utility patent application Ser. No. 14/679,914, filed Apr. 6, 2015, and issued as U.S. Pat. No. 9,149,549. This application is also a continuation-in-part of U.S. Utility patent application Ser. No. 14/679,860, filed Apr. 6, 2015, and issued as U.S. Pat. No. 9,144,618. This application is also a continuation-in-part of U.S. Utility patent application Ser. No. 14/533,814, filed Nov. 5, 2014, and issued as U.S. Pat. No. 8,999,238, and which is a continuation of U.S. Utility patent application Ser. No. 13/779,635, filed Feb. 27, 2013, and issued as U.S. Pat. No. 8,907,304. The contents of this patent application and the patents are incorporated by reference herein in their entirety.

BACKGROUND

The present disclosure is generally directed to a sanitation device and, more particularly, to a sanitation device that includes a source of ultraviolet (UV) radiation that is used to sanitize a surface. Additional embodiments of the present disclosure are directed to methods of sanitizing surfaces using the device.

This disclosure further concerns sanitizing aircraft, particularly aircraft cabins. Further the disclosure concerns sanitizing surfaces at and of locations associated with mass transportation.

The system applies, for instance, to airplanes, and other mass transportation systems, namely vehicles and collection and discharge areas, and assembly locations relating for instance to buses, trains, ferries etc. and other forms of passenger conveyance.

A system and method trolley intended to sanitize the air and surfaces in an aircraft cabin that are commonly contacted by passengers in an effort to minimize the risk of disease spread.

Infectious disease transmission among air travelers is a significant personal and public health concern. Common and potentially serious viral (e.g. Influenza), bacterial (e.g. Methicillin Resistant Staph aureus), and fungal pathogens are typically spread through the air and from mutually contacted surfaces, known as "fomites". Commercial aircraft currently use extensive on-board air filtration and ultraviolet "C" band (UVC) (extrinsic to cabin compartment) technologies to decrease airborne microbes, yet disease transmission continues, suggesting cabin surfaces may play a role.

UVC is an effective germicidal technology not only for air, but for surfaces. However, there is no currently available technology to effectively and efficiently sanitize the surfaces of a passenger aircraft interior. The aircraft interior is never exposed to natural ultraviolet light. Chemical disinfection is labor intensive, with potential harmful residues. Human exposure to UVC can be associated with skin and eye damage and care must be exercised in its use.

SUMMARY

The present disclosure generally relates to a sanitation device for sanitizing surfaces. In accordance with one embodiment of the disclosure, the sanitization device includes a mobile body and a source of UV radiation. The source of UV radiation is mounted to the mobile body, which is configured to travel over a surface. The source of UV radiation is configured to direct UV radiation to the surface at a dosage sufficient to diminish microbial loads to acceptable levels.

Some distinguishing features of the current disclosure include:

- a trolley for negotiating aircraft or similar aisles.
- two arms, that are:
  - laden with UVC sources situated to disperse in a plurality of directions
  - articulated to be laterally extensible over the seat backs and retractable within the trolley footprint.
  - motor controlled and actuated.
  - variably extensible, depending upon the seating configuration.
  - programmable, depending upon the seating configuration.
  - able to function independent of each other.

One utility of this disclosure is self-evident on an intermittent basis in commercial domestic and international routine travel. In the extreme case of a bioterror threat of dispersing particularly lethal microbes via aircraft, this disclosure has the potential of preventing mass casualties.

The current disclosure provides a rapid, safe and effective means of sanitizing the cabin interior by exposure to germicidal UV-C light during routine ground fueling, and maintenance.

Additional and further objects, features, and advantages of the present disclosure will be readily apparent to those skilled in the art.

Other features and benefits that characterize embodiments of the present disclosure will be apparent upon reading the following detailed description and review of the associated drawings.

DESCRIPTION

Figure 1:
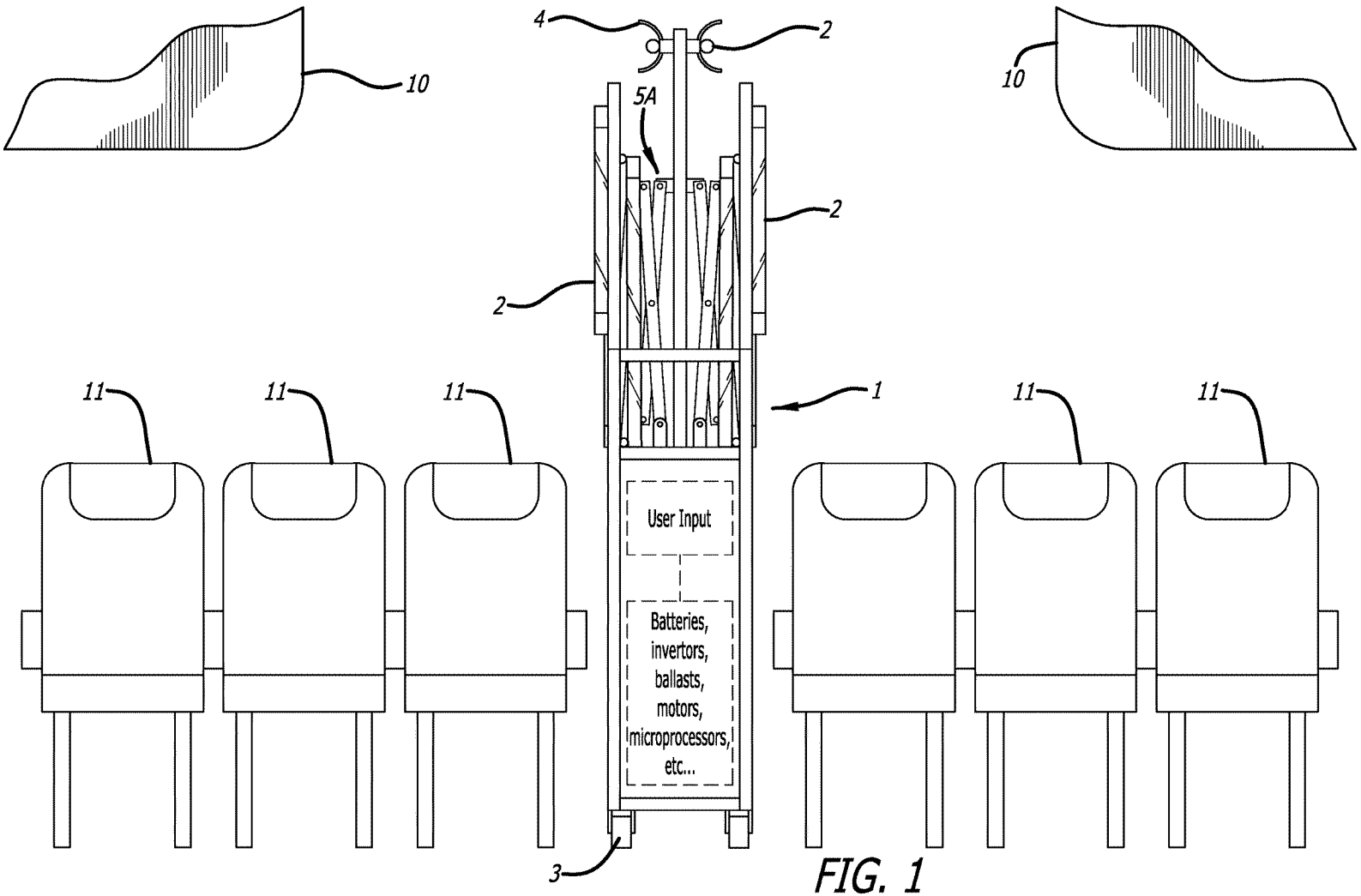
FIG. 1: Front View of Trolley with Arms Embodiment 1 in Stowed/Retracted Positions.
Figure 2:
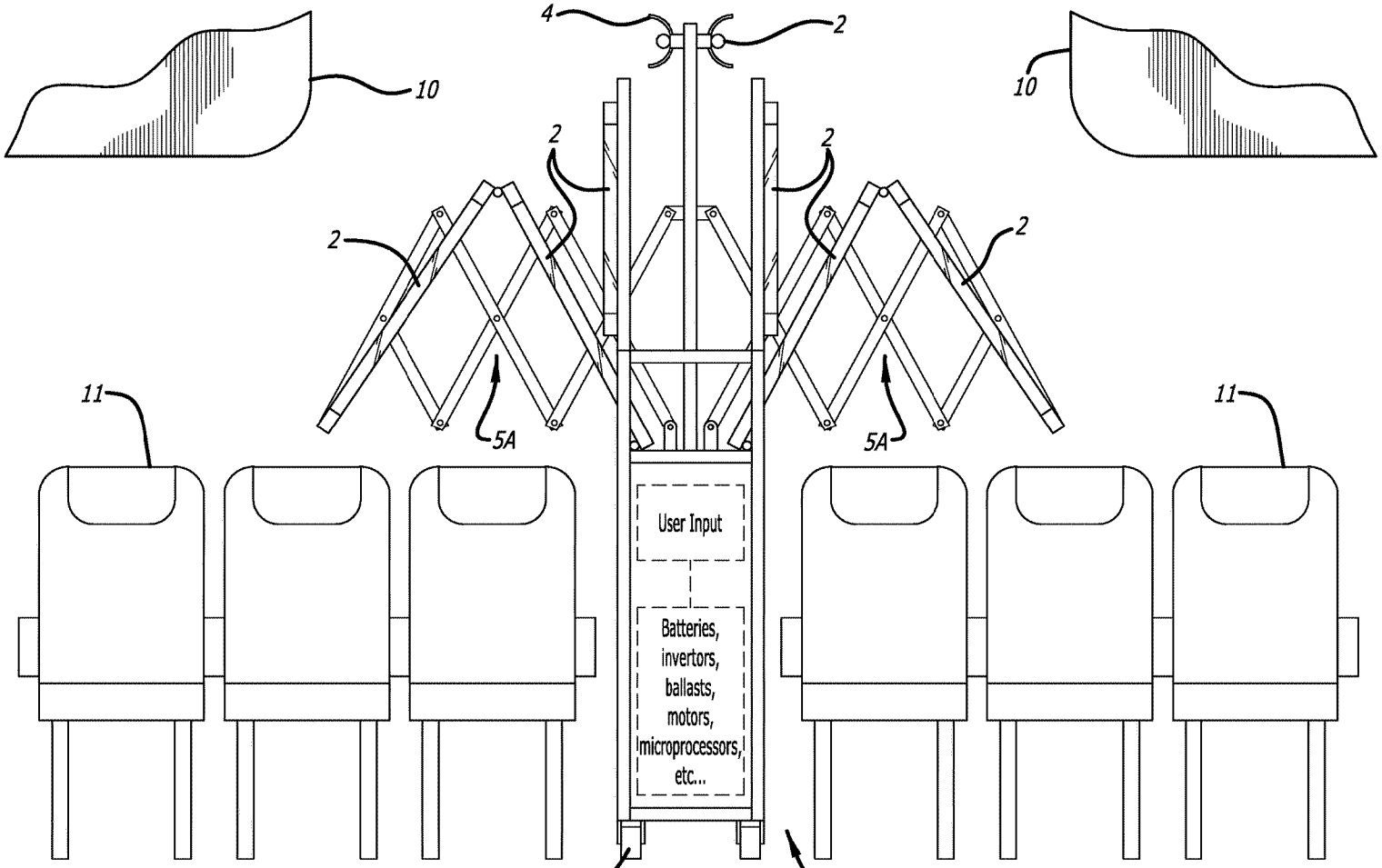
FIG. 2: Front View of Trolley with Arms Embodiment 1 in Partially Extended Positions.
Figure 3:
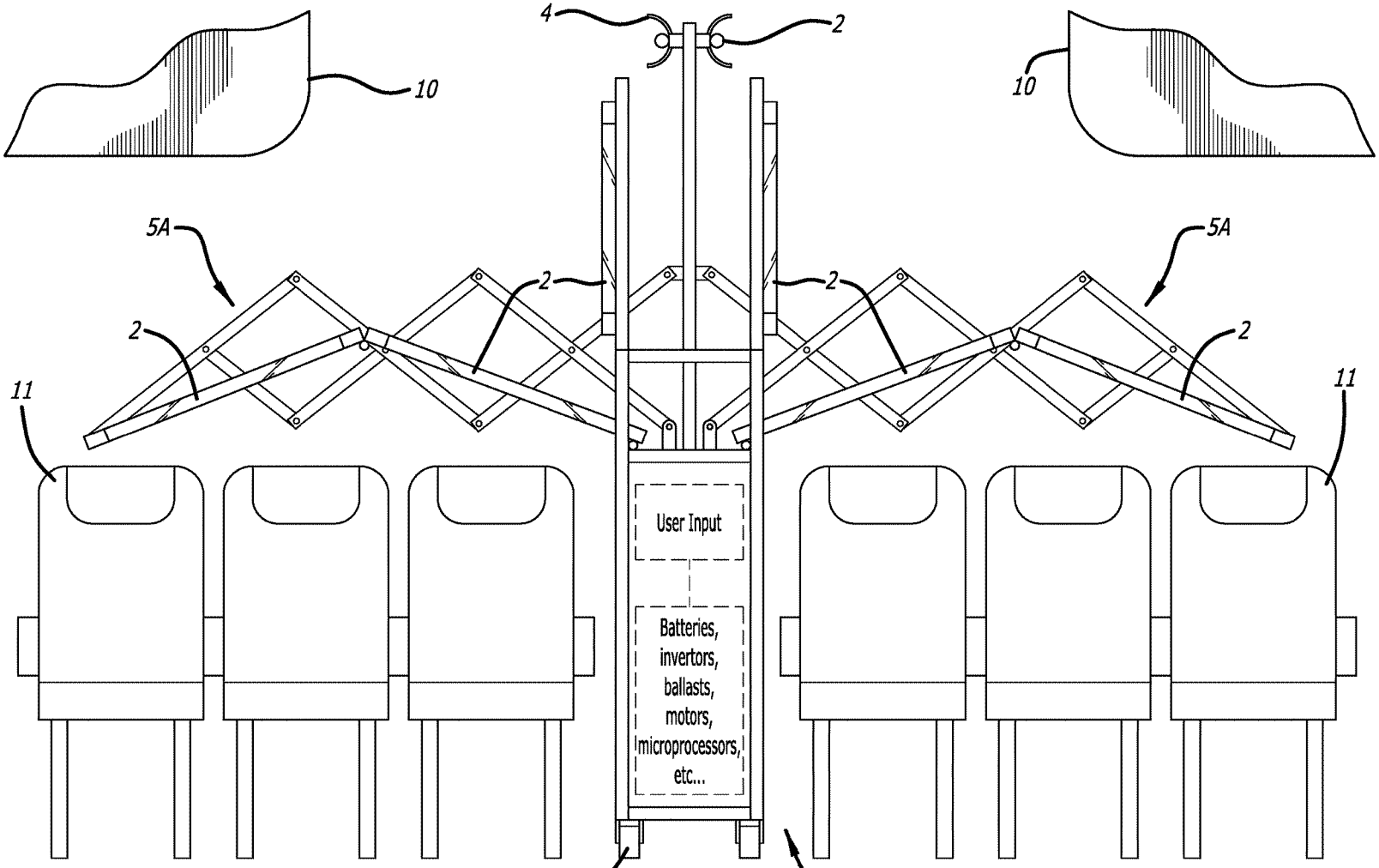
FIG. 3: Front View of Trolley with Arms Embodiment 1 in Fully Extended Positions.
Figure 4:
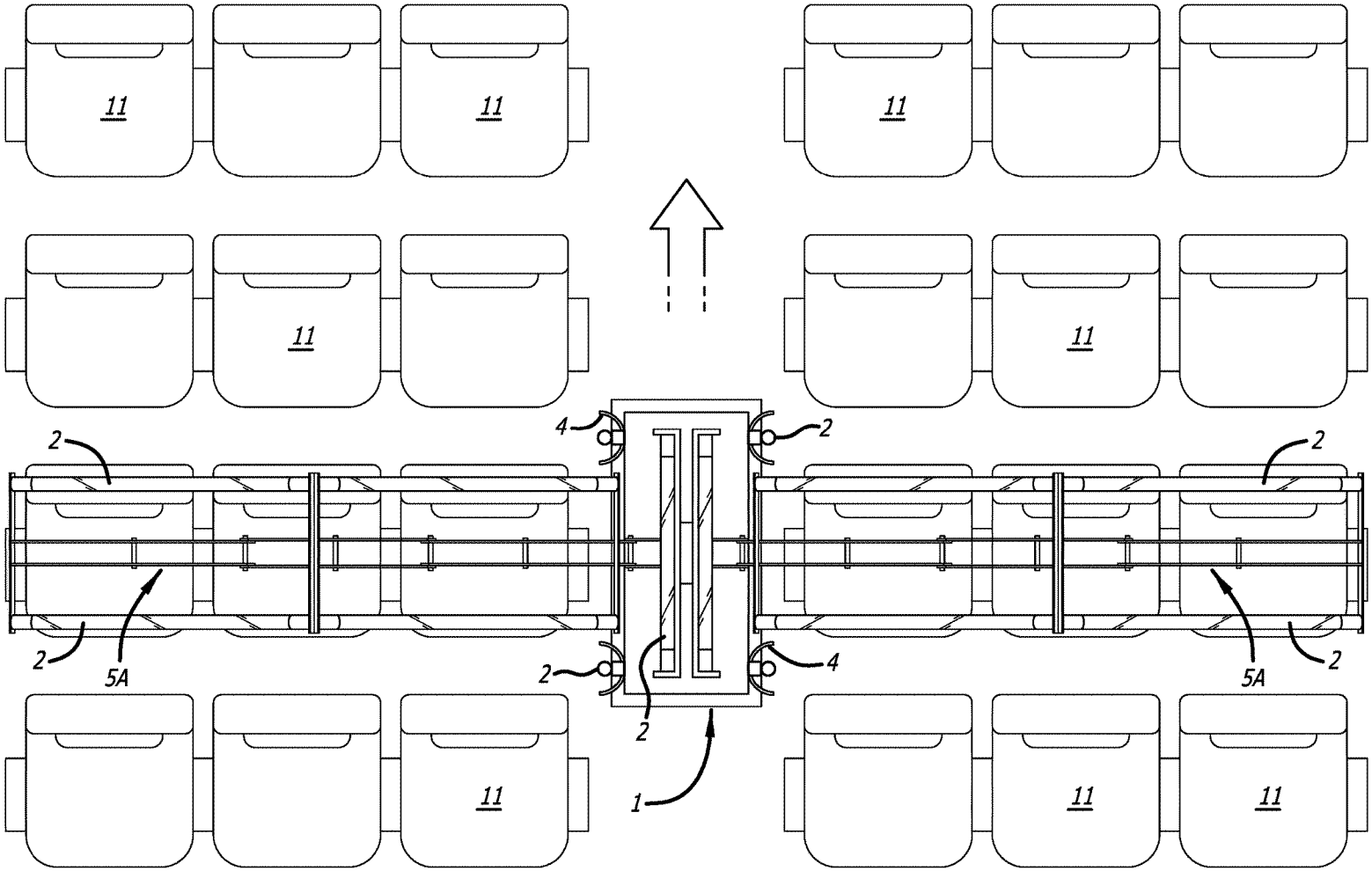
FIG. 4: Top View of Trolley with Arms Embodiment 1 in Fully Extended Positions.
Figure 5:
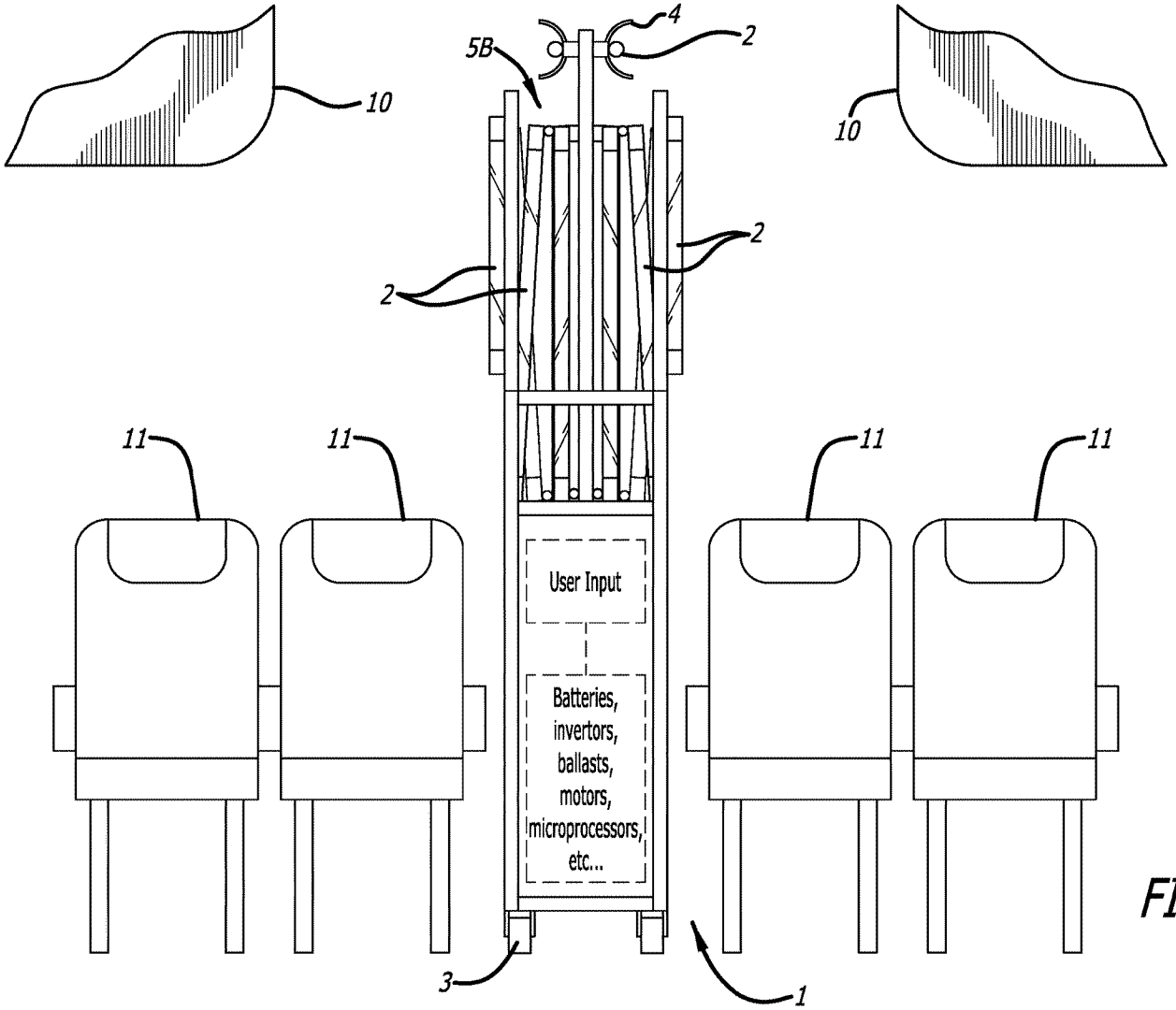
FIG. 5: Front View of Trolley with Arms Embodiment 2 in Stowed/Retracted Positions.
Figure 6:
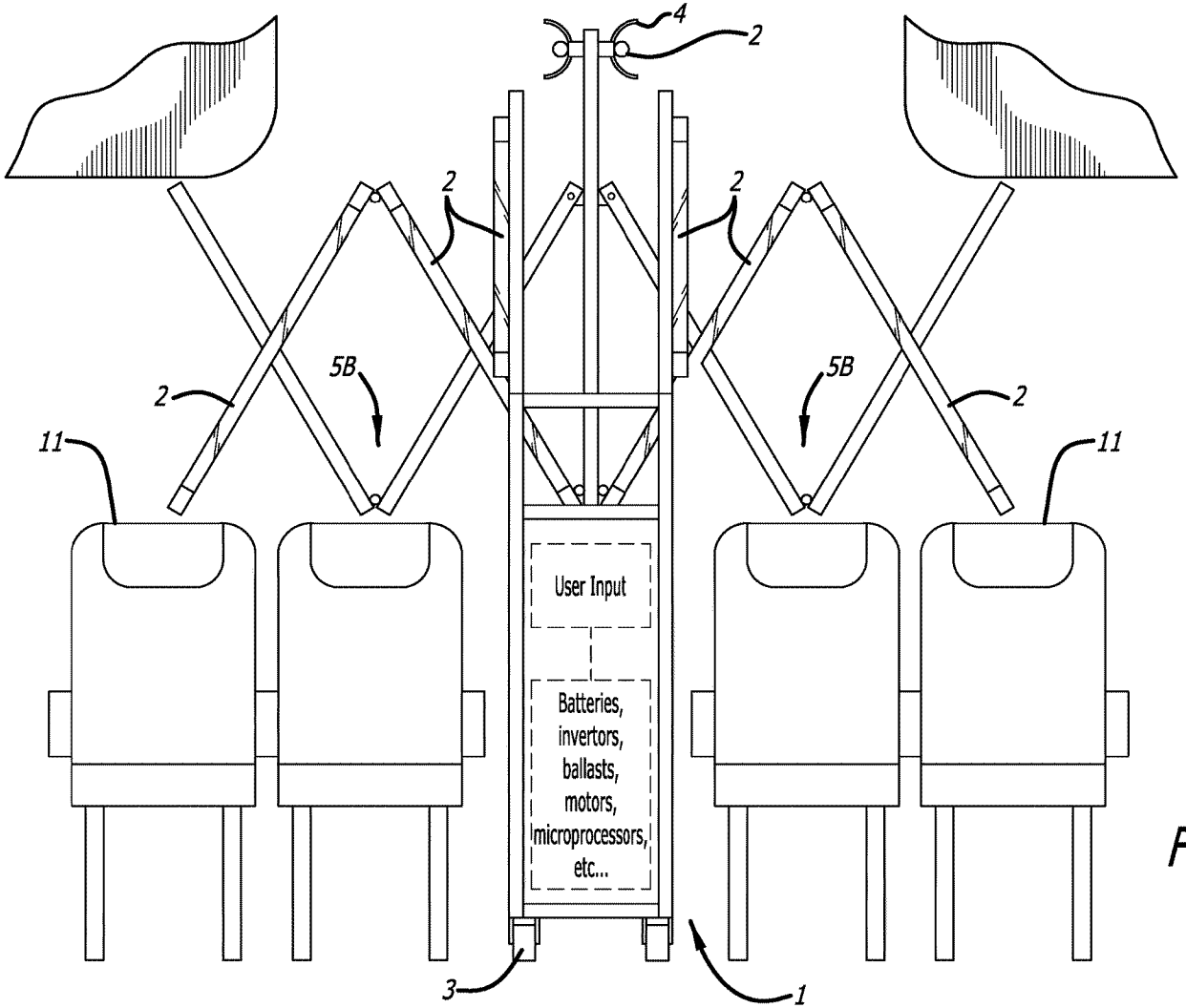
FIG. 6: Front View of Trolley with Arms Embodiment 2 in Partially Extended Positions.
Figure 7:
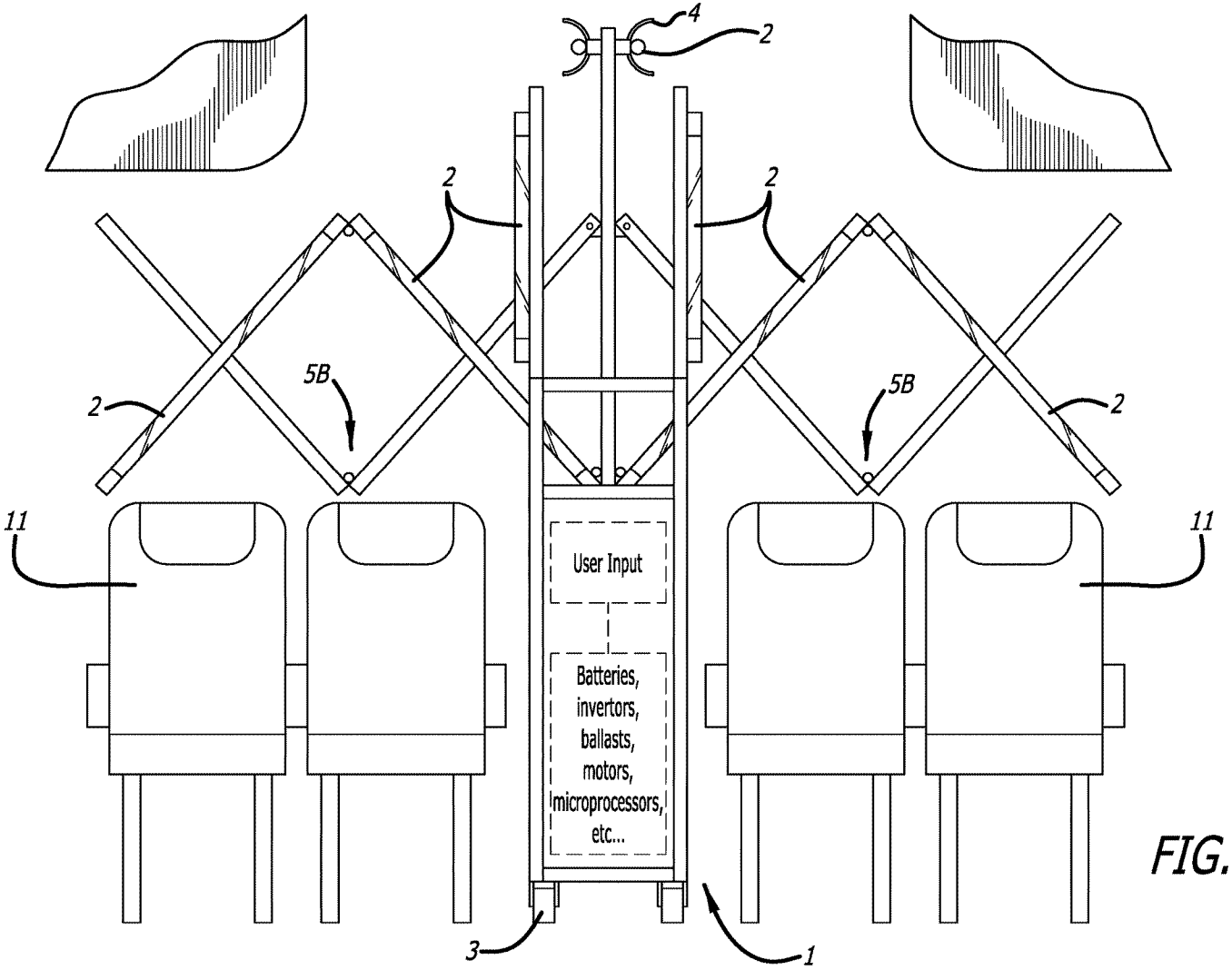
FIG. 7: Front view of Trolley with Arms Embodiment 2 in Greater Partially Extended Positions.
Figure 8:
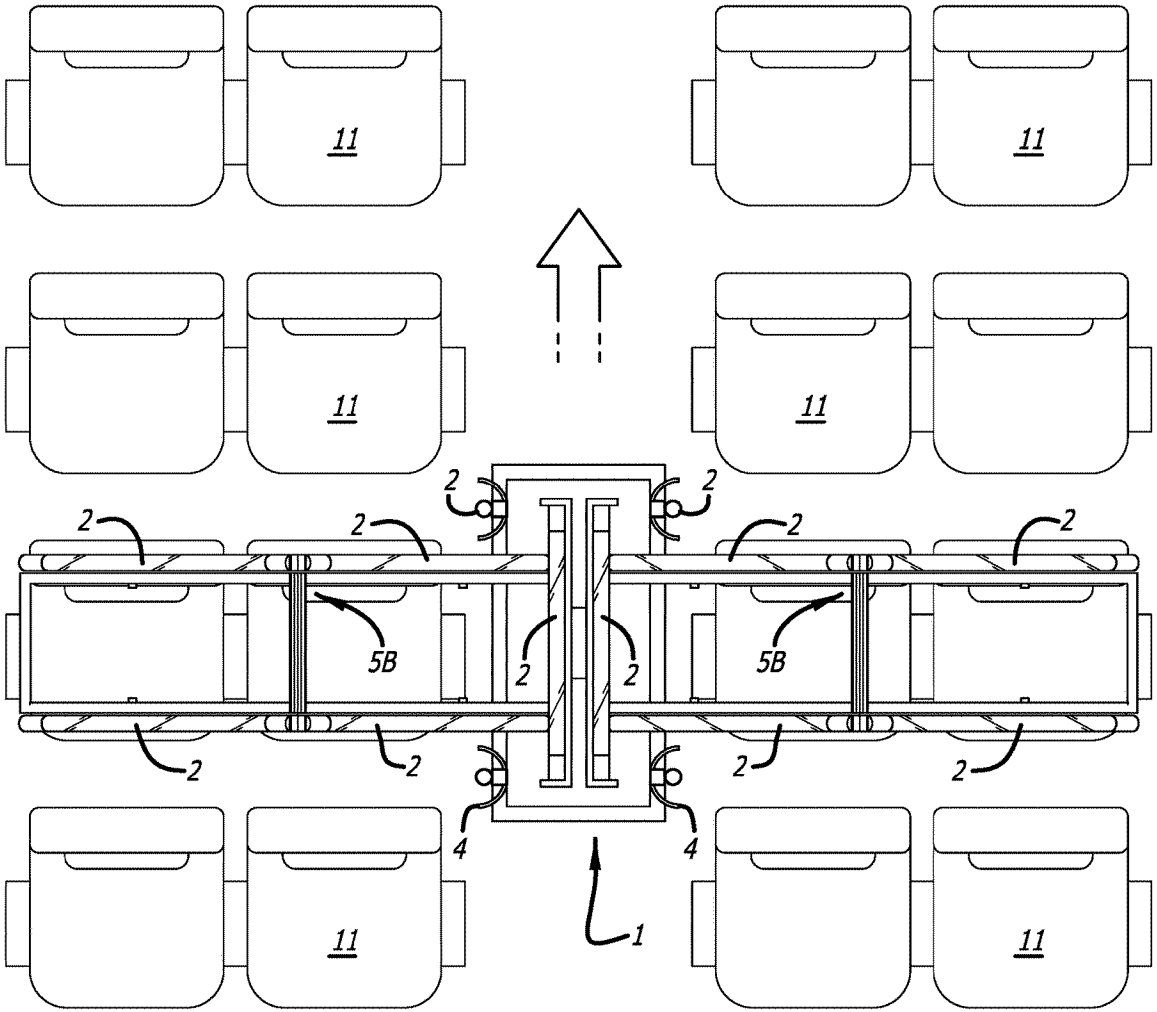
FIG. 8: Top View of Trolley with Arms Embodiment 2 in Fully Extended Positions.

In one form of the disclosure there is a method of sanitizing seat surfaces in an aircraft passenger cabin, the cabin having multiple rows of seats arranged opposite to each other with an aisle between the opposite rows comprising the steps of:

a) providing a sanitization device including a mobile body configured to travel along the aisle of the passenger cabin of the aircraft; the mobile body being composed of at least two separable components, the components being for location one above the other, which when joined together with one above the other, the components form a functional sanitization device;

b) extending a sanitization device laterally from the mobile body across a seat surface, a source of UV radiation being mounted on the sanitization device;

c) moving the sanitization device across a first seat surface;

d) exposing the first seat surface to UV radiation produced by the source;

e) moving the mobile body along the aisle while the device moves over seats surfaces of subsequent seat rows; and f) directing a source of UV radiation to the seat surfaces at a predetermined dosage while the device moves over seats surfaces; the mobile body being powered by a power source on board the mobile device.

Further there is a method of sanitizing seat surfaces in an aircraft passenger cabin, the cabin having multiple rows of seats arranged opposite to each other with an aisle between the opposite rows comprising the steps of:

a) providing a sanitization device including a mobile body configured to travel along the aisle of the passenger cabin of the aircraft; the mobile body being composed of at least two separable components, the components being for location one above the other, which when joined together with one above the other, the components form a functional sanitization device;

b) extending a sanitization device laterally from the mobile body across a seat surface, a source of UV radiation being mounted on the sanitization device;

c) moving the sanitization device across a first seat surface;

d) exposing the first seat surface to UV radiation produced by the source;

e) moving the mobile body along the aisle while the device moves over seats surfaces of subsequent seat rows; and f) directing a source of UV radiation to the seat surfaces at a predetermined dosage; the mobile body being powered by a power source on board the mobile device, providing an articulated arm for seats on one side of the aisle and an articulated arm for seats on the opposite side of the aisle, whereby seats on both sides of the aisle are sanitized as the mobile device moves along the aisle.

Also there is a method of sanitizing surfaces in the seating area of an aircraft passenger cabin, the cabin having multiple rows of seats arranged opposite to each other with an aisle between the opposite rows comprising the steps of:

a) providing a sanitization device including a mobile body configured to travel along the aisle of the passenger cabin of the aircraft; the mobile body being composed of at least two separable components, the components being for location one above the other, which when joined together with one above the other, the components form a functional sanitization device;

b) extending a sanitization device laterally from the mobile body across the seats, a source of UV radiation being mounted on the sanitization device;

c) moving the sanitization device across the seats;

d) exposing surfaces in the passenger cabin to UV radiation produced by the source;

e) moving the mobile body along the aisle while the device moves over surfaces in the cabin; and f) directing a source of UV radiation to the surfaces at a predetermined dosage.

In another form there is a sanitization device for sanitizing a surface inside an aircraft cabin comprising: a mobile body configured to travel over a surface; the mobile body being composed of at least two separable components, the components being for location one above the other, which when joined together with one above the other, the components form a functional sanitization device. A source of UV radiation is mounted to the mobile body and configured to direct UV radiation to the surface at a predetermined dosage; at least an arm mounted to the mobile body. UV lamps are mounted on the arm.

The mobile body is a trolley or cart for negotiating an aircraft aisle. A power source is provided for activating the UV radiation as the trolley or cart moves along the aircraft aisle. The arm is mounted with the mobile body and extendable from the mobile body at a position movable over the seats and the UV lamps are directed to the seat surface. When extended from the mobile body and back into mobile body are above the seat level, wherein the multiple UV lamps are set up to extend over a seat, and wherein the arm for the lamps are movable inwardly relative to each other and towards the trolley and outwardly from the trolley to extend over the seats.

In yet another form there is a sanitization device for sanitizing a surface inside an aircraft cabin comprising: a mobile body configured to travel over a surface; the mobile body is composed of at least two separable components, the components being for location one above the other, which when joined together with one above the other, the components form a functional sanitization device.

A source of UV radiation is mounted to the mobile body and configured to direct UV radiation to the surface at a predetermined dosage; at least one arm mounted to the mobile body.

A UV lamp is mounted on the arm, and the mobile body being a trolley or cart for negotiating an aircraft aisle. The arm is movable from a position of storage with the mobile body to a position to extended from the mobile body wherein in the extended position the arm is operational to effect sanitization.

A power source is provided for activating the UV radiation as the trolley or cart moves along the aircraft aisle. The arm is mounted on the side of the trolley or cart, and the arm includes multiple UV lamps mounted on the arm in spaced relationship with each other thereby in the extended position to cover an increased area to effect sanitation, and wherein the arm is mounted with the mobile body and extendable from the mobile body at a position movable over the seats and the UV lamps are directed to the seat surface.

When extended from the mobile body and back into mobile body are above the seat level, the multiple UV lamps are set up to extend over a seat. The arm for the lamps is movable inwardly and towards the trolley and outwardly from the trolley to extend over the seats.

In a further form there is a sanitization device for sanitizing a surface inside an aircraft cabin comprising: a mobile body configured to travel over a surface. The mobile body is composed of at least two separable components, the components being for location one above the other, which when joined together with one above the other, the components form a functional sanitization device. There is a source of UV radiation configured to direct UV radiation to the surface at a predetermined dosage. There is at least one arm mounted to the mobile body, and UV lamps are mounted on the arm.

The mobile body is a trolley or cart for negotiating an aircraft aisle. A power source for activating the UV radiation as the trolley or cart moves along the aircraft aisle wherein the arm is mounted on the mobile body and extends from the mobile body at least at a height above the seat level of the seat, and preferably between the seat level and the top of the backrest of the seat, or preferably above the top of the back rest of the seat and below overhead bins of the aircraft. The arm for the UV radiation sources is such that the arm is movable towards the trolley during storage action, and when the arm is folded into the trolley, the arm is entirely at a position above the seat level.

The trolley further including multiple spaced UV radiation lamps located in relatively spaced fixed positions in and around the trolley body for projecting UV radiation from the trolley body, and wherein the arm is mounted with the mobile body and extendable from the mobile body at a position movable over the seats and the UV lamps are directed to the seat surface. When extended from the mobile body and back into mobile body it is above the seat level. Multiple UV lamps are set up to extend over a seat, and wherein the arm for the lamps are movable inwardly relative to each other and towards the trolley and outwardly from the trolley to extend over the seats.

In a further form there is a sanitization device for sanitizing a surface inside an aircraft cabin comprising: a mobile body configured to travel over a surface; the mobile body is composed of at least two separable components, the components being for location one above the other, which when joined together with one above the other, the components form a functional sanitization device.

A source of UV radiation is mounted to the mobile body and configured to direct UV radiation to the surface at a predetermined dosage. There is at least one arm mounted to the mobile body, and UV lamps mounted on the arm.

The mobile body is a trolley or cart for negotiating an aircraft aisle. There is a power source for activating the UV radiation as the trolley or cart moves along the aircraft aisle, and wherein the arm is mounted with the mobile body and extendable from the mobile body.

In one version of the system and method, with the sides open, the arms and/or wings can essentially fully deploy independently of the telescoping position. In this form, the arms can be deployed and/or stowed with the wing assembly all the way down, all the way up or anywhere in between. This feature is useful, when sanitizing the lavatory, as the toilet is quite low and the arms deploy with the wing assembly down. Then, while the wing is in the lavatory, the telescoping mechanism is programmed to rise to also sanitize the sink, countertop, valves, flush controls, etc. The wing and the arm are components which are the same or interchangeable.

In another form this is effected by telescoping vertically into and out of the body, and when out of the body, are extendible outwardly from the body to a position movable over the seats and the UV lamps are directed to the seat surface. When extended from the mobile body and back into mobile body are above the seat level. The multiple UV lamps are set up to extend over a seat, and wherein the arm for the lamps is movable inwardly towards the trolley and outwardly from the trolley to extend over the seats.

The device can include the mobile body which is composed of at least three separable components, the components are for location one above the other, which when joined together with one above the other, the components form a functional sanitization device.

One component is a module being a cart-including a chassis, wheels, motors. A second component is a module being a base removably attachable to the cart and selectively including a covered frame, lamps with reflective housings and a telescoping mechanism, and including electronics components fitting within the base including a controller processor, and ballast, and including a battery pack mounted to the base. A third component is a module being a wing assembly for fitting into the base with a telescoping mechanism that allows vertical translation.

The ballasts can be in the body. In another form at least some of the ballasts are located in the wing assembly module.

The method includes employing the device to sanitize at least one an aircraft lavatory area or aircraft galley area. The body supports sanitization lamps on a base of the body.

When the device is employed to sanitize at least one an aircraft lavatory area or aircraft galley area, the sanitizing of the lavatory area with the sanitization device operates with an arm in the lavatory area, and is directed toward a toilet, and also is for moving to expose a countertop, and a sink in the lavatory.

When the device is employed to sanitize at least one an aircraft lavatory area or aircraft galley area, the sanitizing of the galley area is effected with the sanitization device operating with an arm in the galley area, and directed toward a countertop and an upper cabinet in the galley area.

Further, there is a method of sanitizing seat surfaces in a location being related to a public mass transportation vehicle and including a passenger area of the location the area having multiple rows of seats arranged opposite to each other with an aisle between the opposite rows comprising the steps of:

a) providing a sanitization device including a mobile body configured to travel along the aisle of the passenger area;
b) extending a sanitization device laterally from the mobile body across a seat surface, a source of UV radiation being mounted on the sanitization device;
c) moving the sanitization device across a first seat surface;
d) exposing the first seat surface to UV radiation produced by the source;
e) moving the mobile body along the aisle while the device moves over seats surfaces of subsequent seat rows; and
f) directing a source of UV radiation to the seat surfaces at a predetermined dosage while the device moves over seats surfaces; the mobile body being powered by a power source on board the mobile device.

Also, there is a method of sanitizing seat surfaces in a location being related to a public mass transportation vehicle and including a passenger area of the location, the area having multiple rows of seats arranged opposite to each other with an aisle between the opposite rows comprising the steps of:

a) providing a sanitization device including a mobile body configured to travel along the aisle of the passenger area;
b) extending a sanitization device laterally from the mobile body across a seat surface, a source of UV radiation being mounted on the sanitization device;
c) moving the sanitization device across a first seat surface;

d) exposing the first seat surface to UV radiation produced by the source;

e) moving the mobile body along the aisle while the device moves over seats surfaces of subsequent seat rows; and f) directing a source of UV radiation to the seat surfaces at a predetermined dosage; the mobile body being powered by a power source on board the mobile device, providing an arm for seats on one side of the aisle and an arm for seats on the opposite side of the aisle, whereby seats on both sides of the aisle are sanitized as the mobile device moves along the aisle.

Yet further, there is a method of sanitizing seat surfaces in a location being related to a public mass transportation vehicle and including a passenger area of the location, the area having multiple rows of seats arranged opposite to each other with an aisle between the opposite rows comprising the steps of:

a) providing a sanitization device including a mobile body configured to travel along the aisle of the passenger area;

b) extending a sanitization device laterally from the mobile body across the seats, a source of UV radiation being mounted on the sanitization device;

c) moving the sanitization device across the seats;

d) exposing surfaces in the passenger area to UV radiation produced by the source;

e) moving the mobile body along the aisle while the device moves over surfaces; and f) directing a source of UV radiation to the surfaces at a predetermined dosage.

The present disclosure generally relates to a sanitization device that utilizes a source of UV radiation to provide a means for sanitizing a surface. As will be discussed below in greater detail, embodiments of the sanitization device include a source of UV radiation in combination with a mobile body, or a housing for handheld operation. Additional embodiments of the present disclosure relate to methods of sanitizing surfaces using the sanitization devices of the present disclosure.

In accordance with another embodiment of the disclosure, the sanitization device includes a mobile body, a surface cleaning component, and a source of UV radiation. The surface cleaning component and the source of UV radiation are mounted to the mobile body, which is configured to travel over a surface. The surface cleaning component is configured to engage the surface and the source of UV radiation is configured to direct UV radiation to the surface.

In accordance with yet another embodiment of the disclosure, the sanitization device includes a housing, a source of UV radiation, and a sensor. The source of UV radiation is contained in the housing and positioned to transmit UV radiation through an opening in the housing. The sensor is configured to detect when the source is within a predetermined distance from a surface to be sanitized.

Additional embodiments of the present disclosure are directed to methods of using the above-identified sanitization devices to sanitize a surface.

A sanitization device for sanitizing a surface inside an aircraft cabin comprises a mobile body configured to travel over a surface. There is a source of UV radiation mounted to the mobile body and configured to direct UV radiation to the surface at a predetermined dosage. There are at least two articulated arms mounted to the mobile body, and UV lamps are mounted respectively on the arms. The mobile body is a trolley or cart for negotiating an aircraft aisle.

In another form there is a sanitization device for sanitizing a surface inside an aircraft cabin. There is a mobile body configured to travel over a surface; and a source of UV radiation mounted to the mobile body and configured to direct UV radiation to the surface at a predetermined dosage. At least one arm is mounted to the mobile body, and a UV lamp is mounted on the arm. The mobile body is a trolley or cart for negotiating an aircraft aisle.

The arm is movable from a position of storage with the mobile body to a position to extend from the mobile body wherein in the extended position the arm is operational to effect sanitization.

In one form each arm is for independent operation.

There are means for controlling motion of the arms over and about the aircraft surfaces, such surfaces including seats of the aircraft.

The arms are mounted with the mobile body and extendable from the mobile body at a position above the back rest of seats. The arms are movable over the seats and the UV lamps are directed to the seat surface as well as above the seats, and toward the interior sides of the fuselage.

The arm or arms are mounted with the mobile body and extendable from the mobile body at a position essentially solely above seats of an aircraft.

A surface cleaning component can be mounted to the mobile body and configured to engage the surface on which the mobile body travels.

The device includes a self-contained powering unit for powering the UV source.

The device can include a sensor for measuring the distance and or power the UV lamps relative to the surface and controlling the amount of and distance of the lamps from the surface and/or UV energy transmitted to the surface. Sensors can be provided for collision avoidance. Sensors cab sense a human being and shut down the UVC.

There is a method of sanitizing the seat surface in an aircraft cabin comprising the following steps. A sanitization device is provided to include a mobile body configured to travel along an aisle of an aircraft, and there is step of sanitizing with a device extending from the mobile device extendible across the seat surface.

There can be a surface cleaning component mounted to the mobile body and configured to engage the surface.

A source of UV radiation mounted to the mobile body is moved so that the sanitization device is directed across the seat surface. The seat surface is exposed to UV radiation produced by the source, and the mobile body is moved along an aisle while the device travels over multiple seat surfaces.

A source of UV radiation mounted to the mobile body is directed to the seat surfaces at a predetermined dosage; extending at least one arm mounted to the mobile body with UV lamps mounted on the arm over the seats as the mobile body travels along an aircraft aisle. The mobile body is powered by a power source on board the mobile device.

The arm or arms are mounted on the mobile body and extend from the mobile body at least at a height above the seat level of the seat, and preferably between the seat level and the top of the backrest seat. The arms are preferably between the top of the backrest and the overhead bins.

A method of sanitizing includes a process wherein as the trolley moves on wheels along an aisle of an aircraft cabin, the arm is extended for movement in a space between the top of the cabin and above the top of backrest of the seats.

A method of sanitizing includes a process wherein as the trolley moves on wheels progressively along an aisle of an aircraft cabin, the arm is extended for movement in a space between the overhead bin/top of the cabin progressively above the top of backrest of the seats and the seat portions of the seats.

A significant part of the fixed costs of the robot can be in the automation and autonomy. The batteries, sensors, actuators and programming with onboard computers really add up, even with volume production. In another form of the disclosure, there can be a unit hand operated, pushed down the aisle by hand, wings deployed and stowed by hand. There can be a plug in version with long extension cords that a human can keep from tangling. The operator can be completely protected with lightweight skin and eye protective gear. Yet another form is a model remotely controlled by an operator standing nearby. Such applications could be in in different environments, namely beyond an aircraft cabin.

A significant part of the fixed costs of the robot can be in the automation and autonomy. The batteries, sensors, actuators and programming with onboard computers really add up, even with volume production. In another form of the disclosure, there can be a unit hand operated, pushed down the aisle by hand, wings deployed and stowed by hand. There can be a plug in version with long extension cords that a human can keep from tangling. The operator can be completely protected with lightweight skin and eye protective gear. Yet another form is a model remotely controlled by an operator standing nearby. For instance there can also be an Pressure sensor; Ultrasonic sensor; Humidity Sensor; Gas Sensor; PIR Motion Sensor; Acceleration sensor; or Displacement sensor. Such applications could be in in different environments, namely beyond an aircraft cabin. An application could be in in different environments, namely beyond an aircraft cabin.

Some different components of the system are set out:

1) Trolley
2) UVC source (lamp)
3) Trolley wheels
4) reflector
5) arm
6) arm extension retraction mechanism
7) rollers
8) hinges
9) guy wire
10) overhead bins
11) aircraft seats
12) light
13) vent
14) control
15) lavatory
16) galley The trolley (1) has a "footprint" similar to that of a standard food/beverage trolley used on aircraft, but is of substantially greater height. The trolley has wheels (3), at least one of which is connected to a motor and at least one of which has a navigation mechanism. The motor and navigation mechanism are connected to an on-board microprocessor controller. There are proximity sensors, not illustrated, along the sides, fore and aft surfaces also connected to the controller.

Ultraviolet "C" (UVC) sources (2) are incorporated into all exterior fore, aft and side, and bottom surfaces of the trolley and located in a manner to maximize exposure of the aircraft interior surfaces. Reflectors (4) are utilized to maximize effective UVC output.

UVC laden "arms" (5) are connected to the trolley in such a manner to be variably laterally extensible above the aircraft seats (11) and below the overhead storage bins (10). These arms (5) may be retracted and stowed within the footprint of the trolley (1) for storage and when maneuvering the trolley (1) into position and on/off the aircraft. UVC source lamps (2) are also located in a sufficiently elevated position to expose the overhead storage bins (10).

Figure 9:
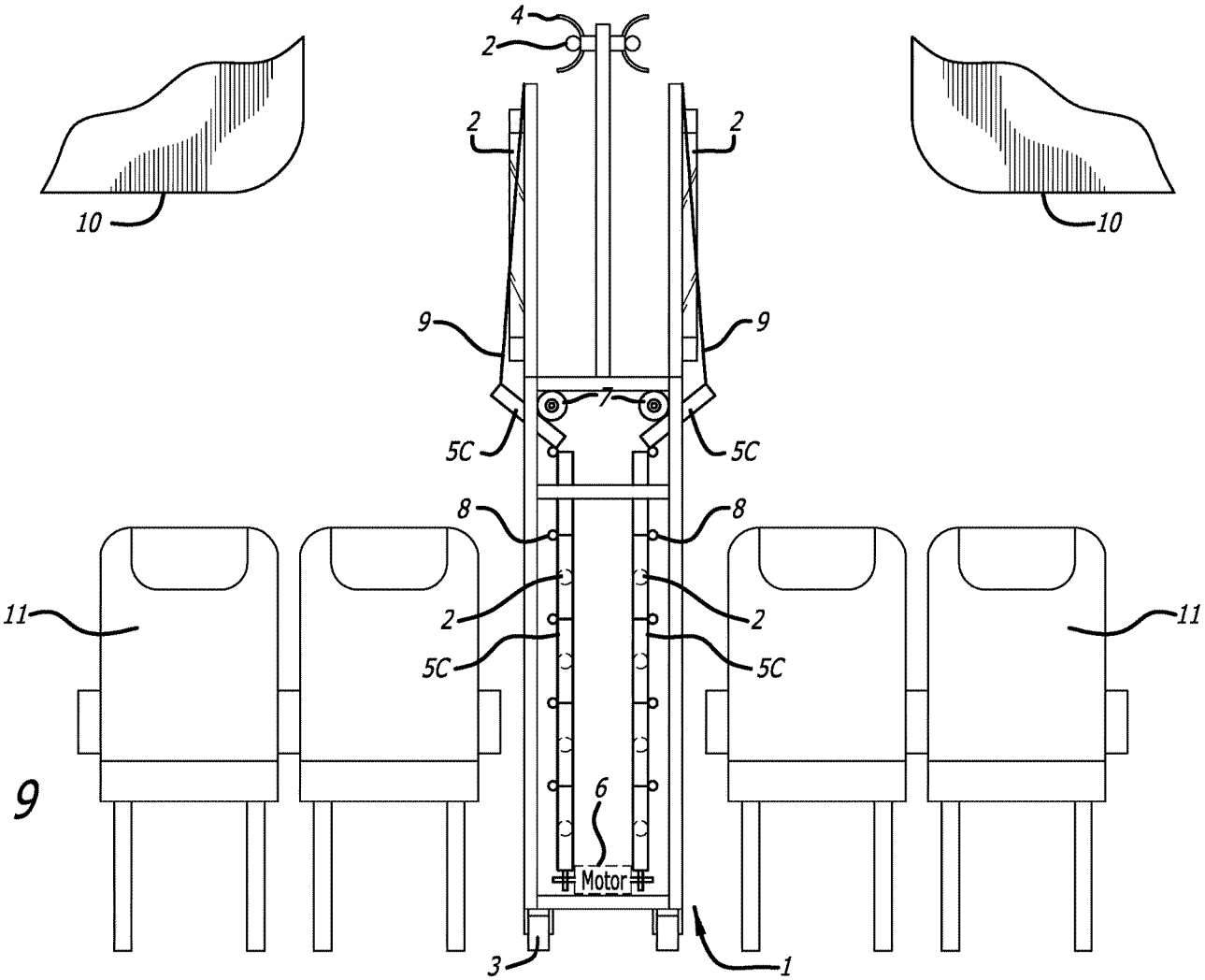
FIG. 9: Front View of Trolley with Arms Embodiment 3 in Stowed/Retracted Positions.
Figure 10:
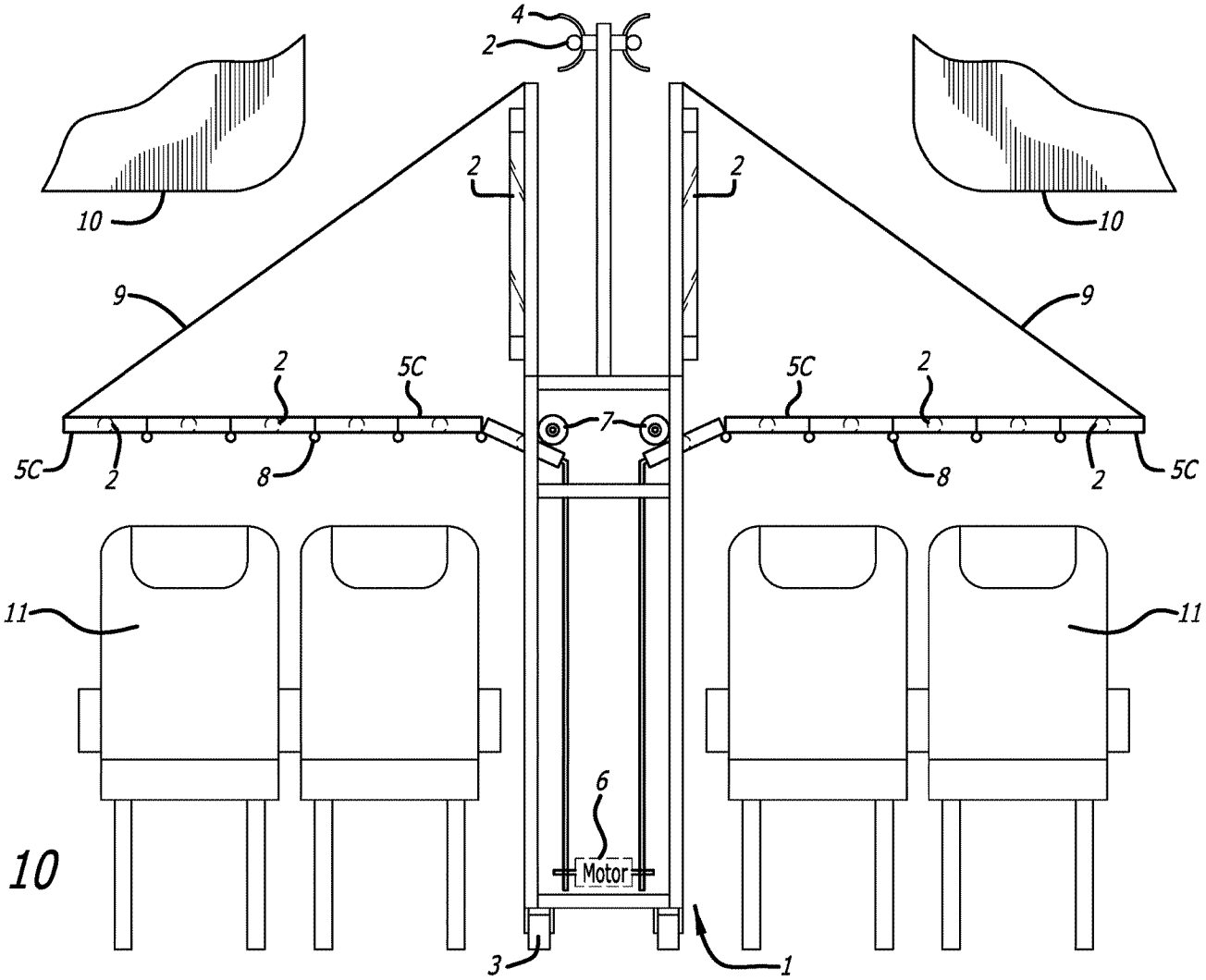
FIG. 10: Front View of Trolley with Arms Embodiment 3 in Fully Extended Positions.
Figure 11:
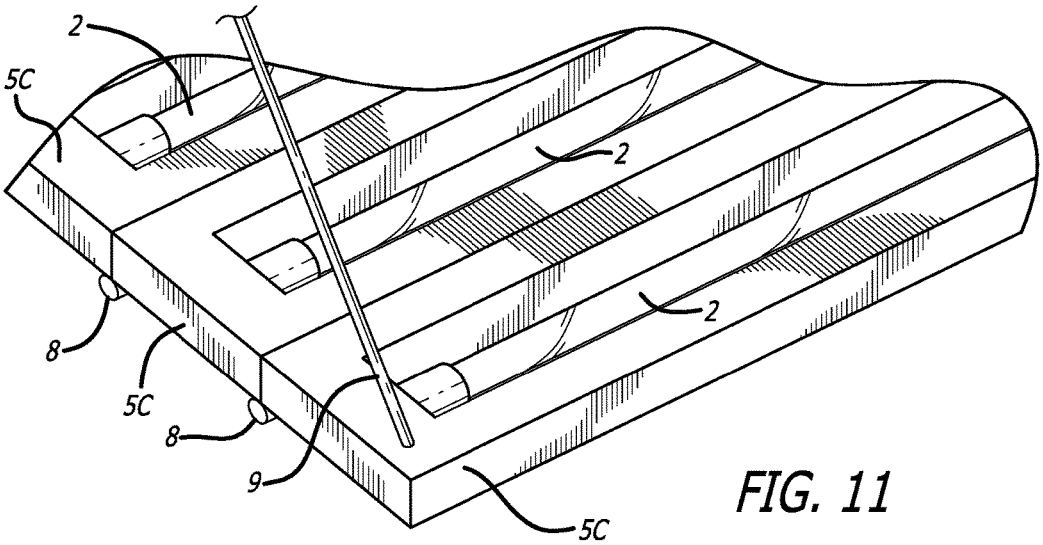
FIG. 11: Detail of Arm Embodiment 3 showing Lamps within Arm.
Figure 12:
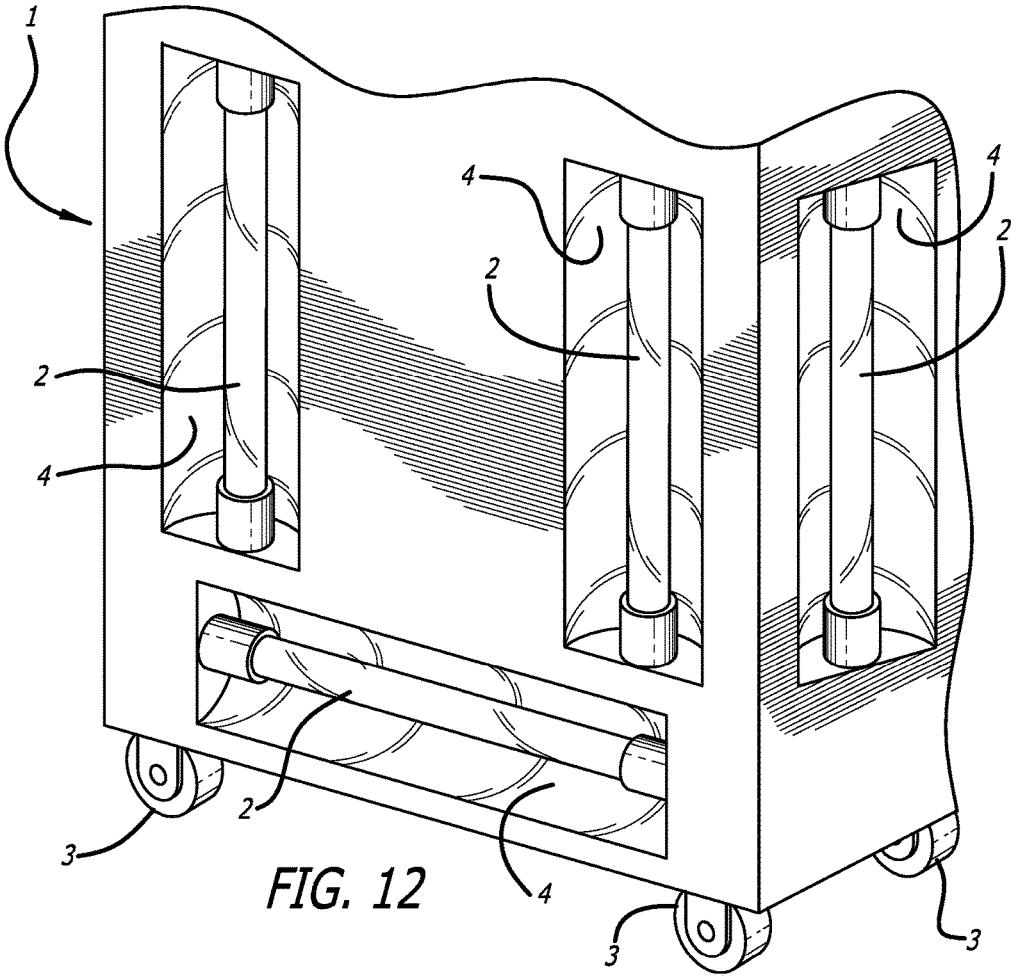
FIG. 12: Trolley Body with Recessed Lamps and Reflectors.
Figure 13:
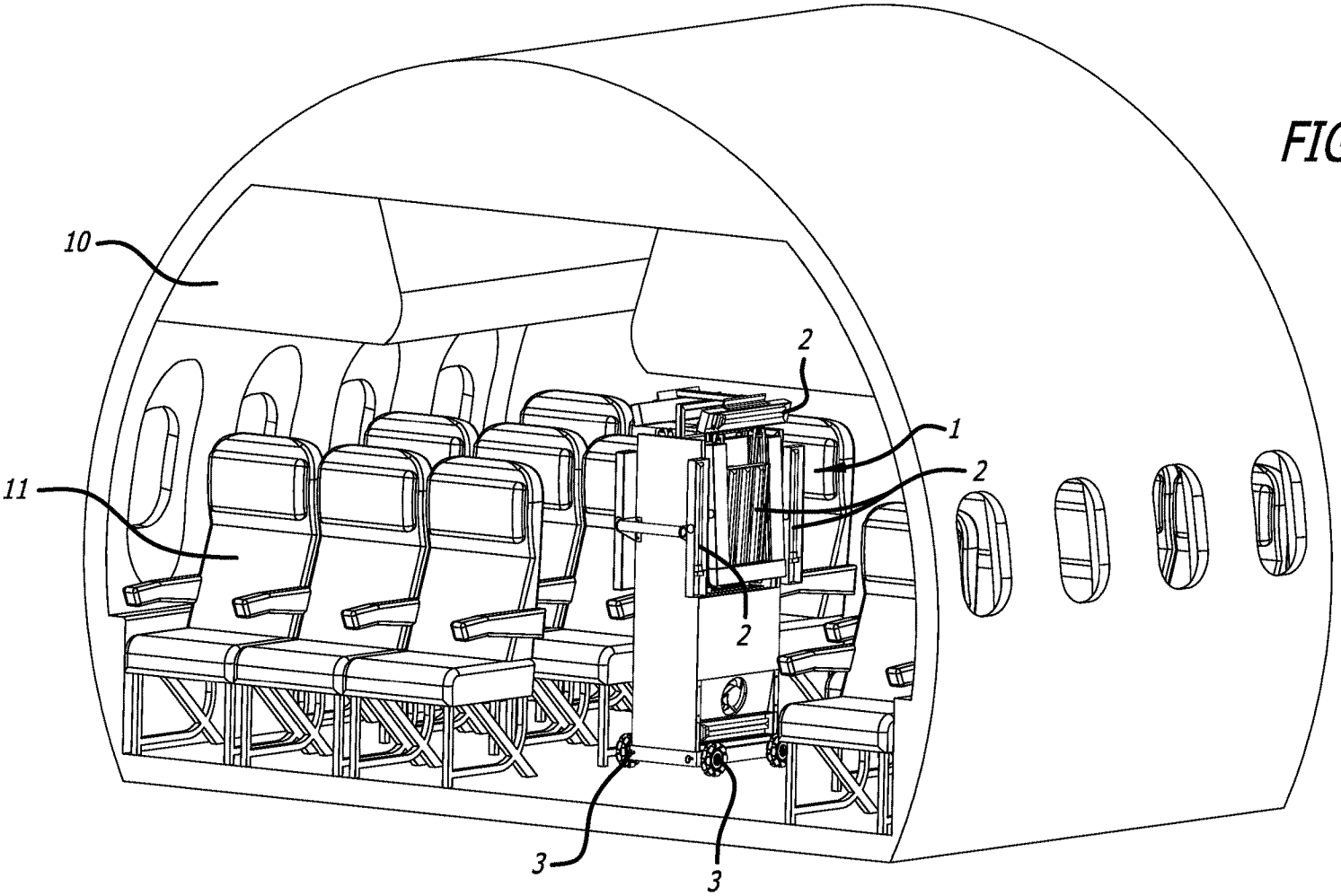
FIG. 13: Perspective view showing a Trolley with arms folded in an aircraft aisle between rows of seats.
Figure 14:
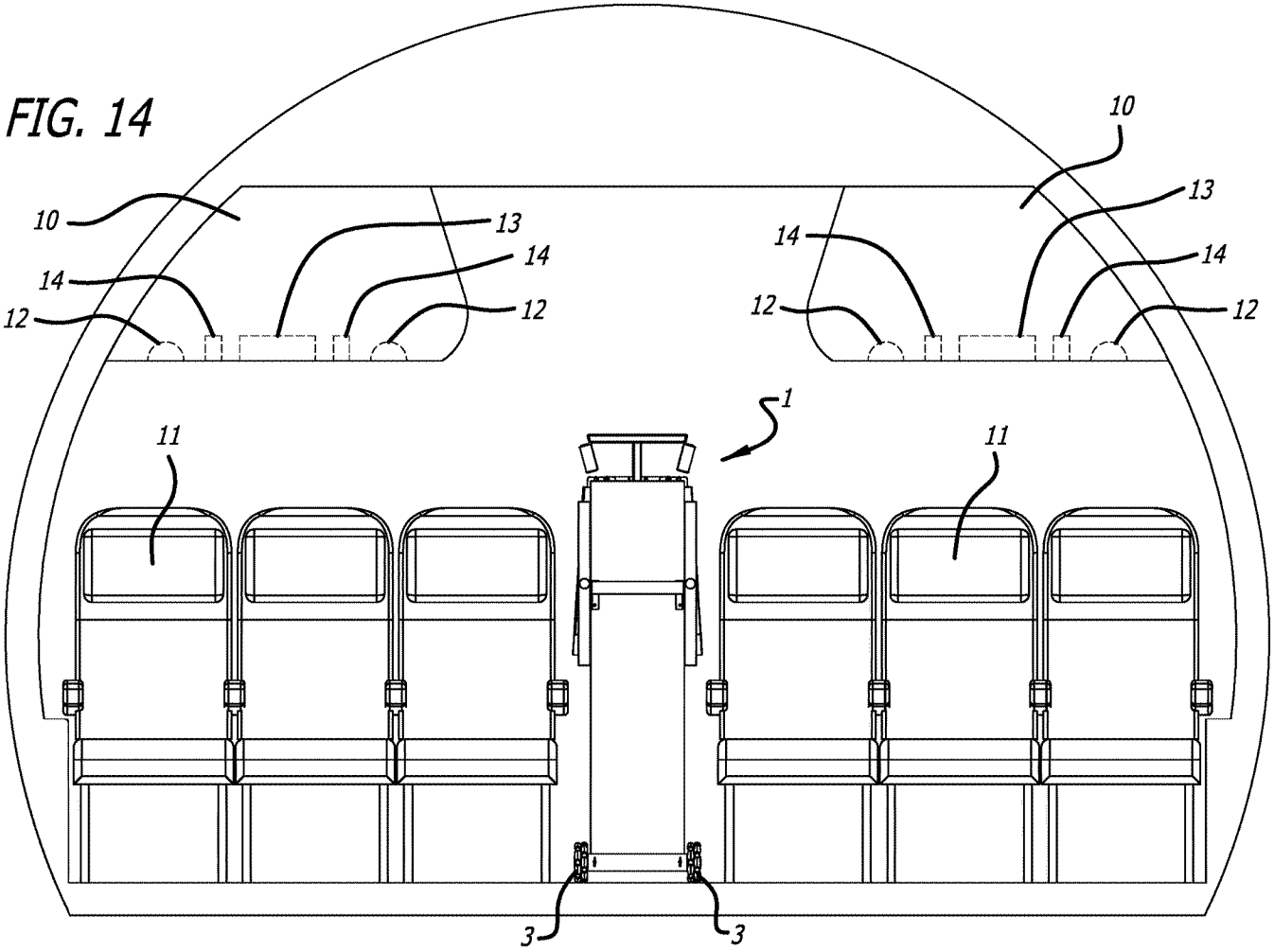
FIG. 14: Front view showing a Trolley with arms folded in an aircraft aisle between rows of seats and also showing the overhead bins and showing exemplary air vents, lights, and controls.
Figure 15:
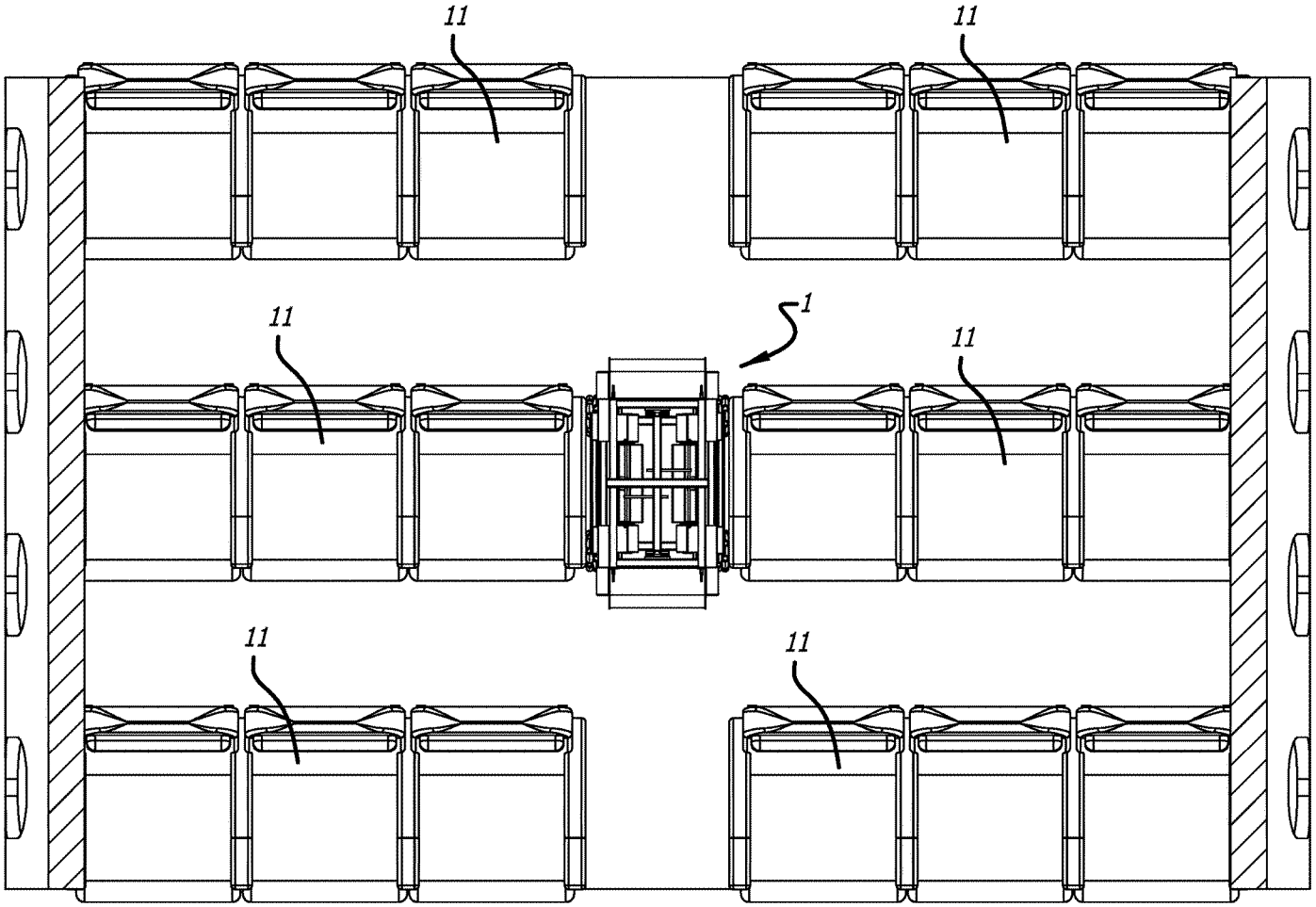
FIG. 15: Top view showing a Trolley with arms folded in an aircraft aisle between rows of seats.
Figure 16:
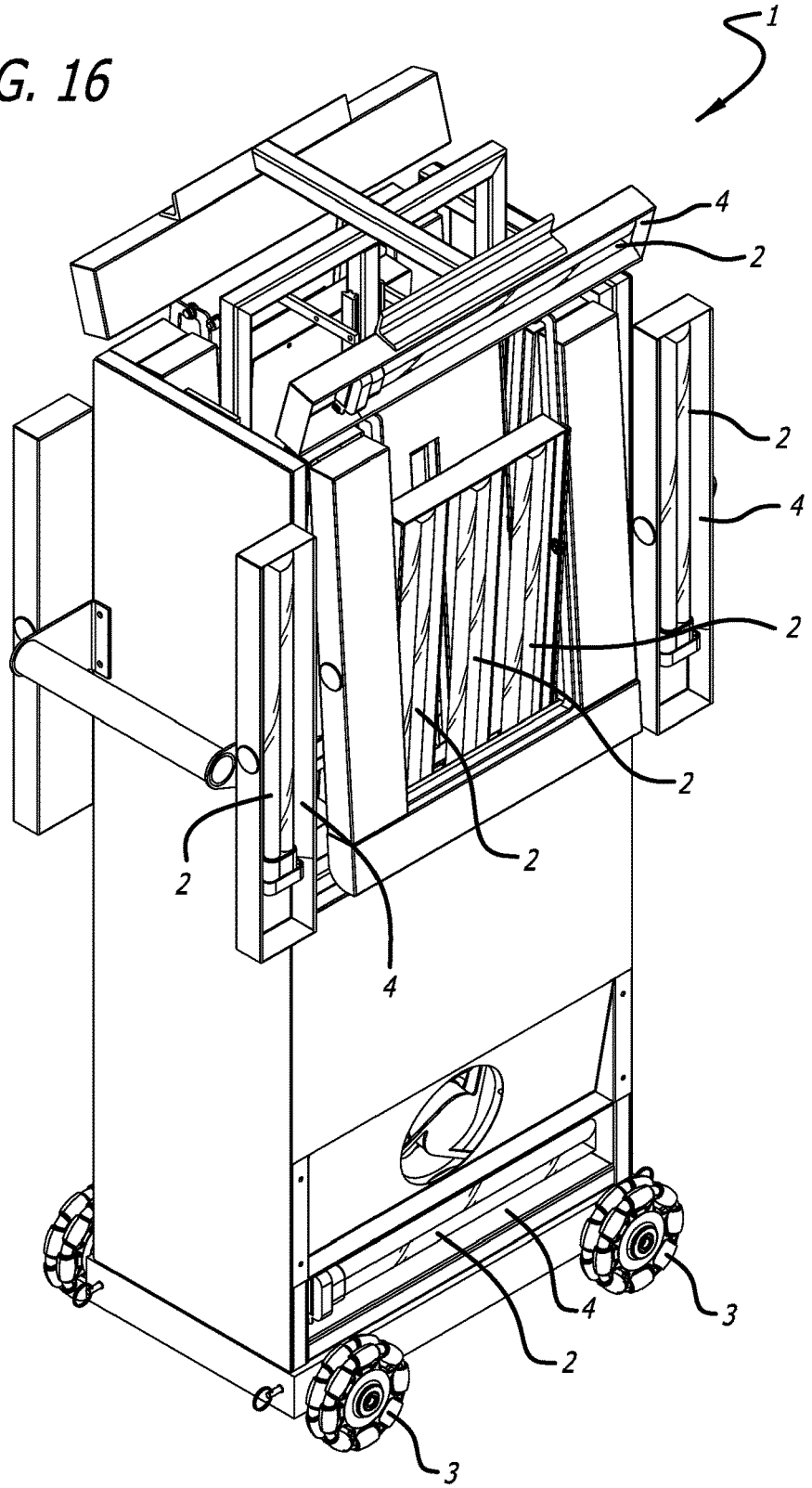
FIG. 16: Perspective view showing a Trolley with arms within and folded on the sides of the trolley body. Also there are vertically arranged fixedly mounted UV lamps mounted on the corners of the trolley and for directing the UVC light outwardly and transversely towards the area at the same height as the trolley and adjacent to the trolley. The navigation wheels on the trolley mounted on the outer perimeter of the body of the trolley.
Figure 17:
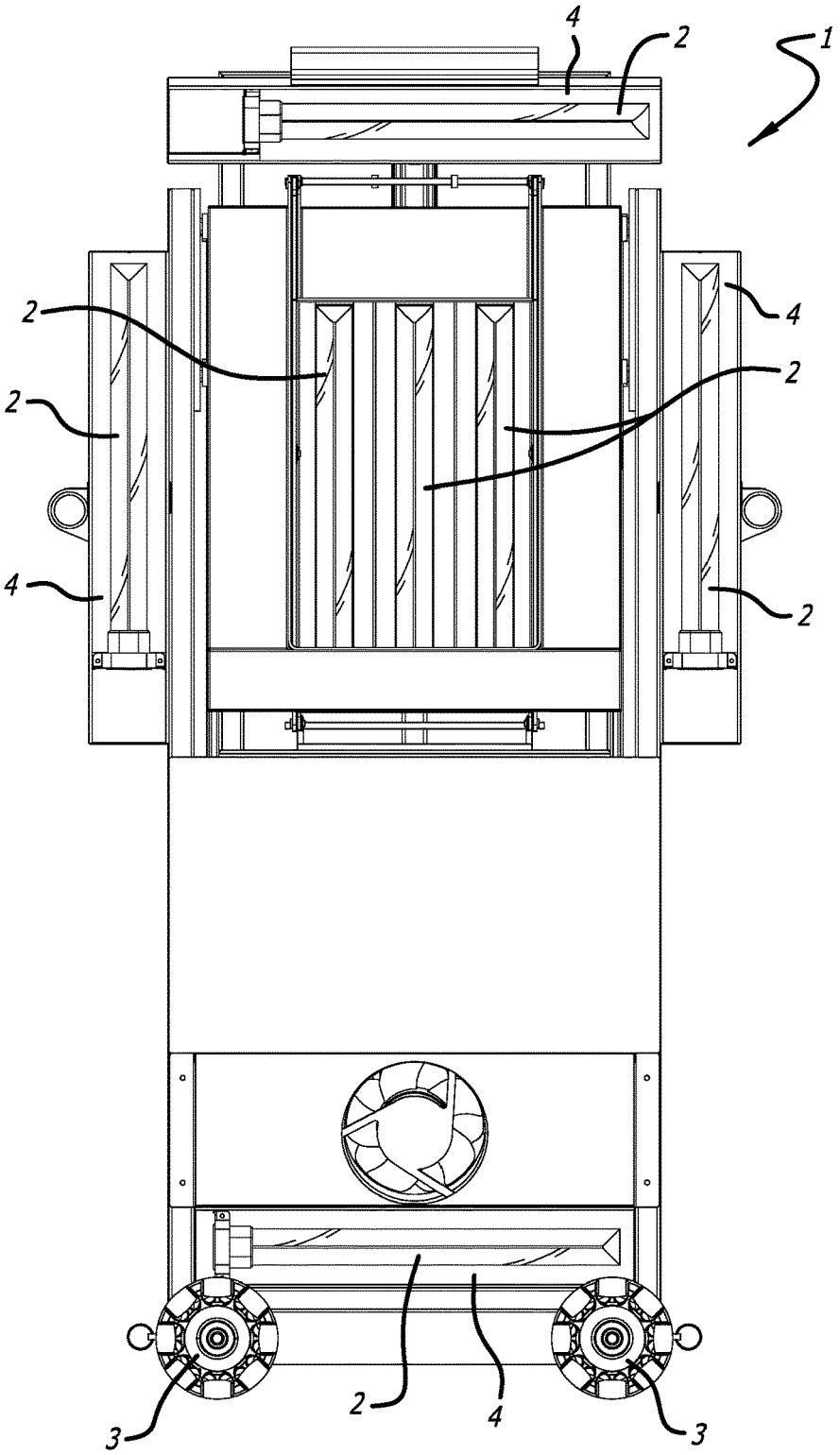
FIG. 17: Side view showing a Trolley with arms folded on the sides of the trolley body, and showing the vertical UVC lights and navigation wheels on the trolley.
Figure 19:
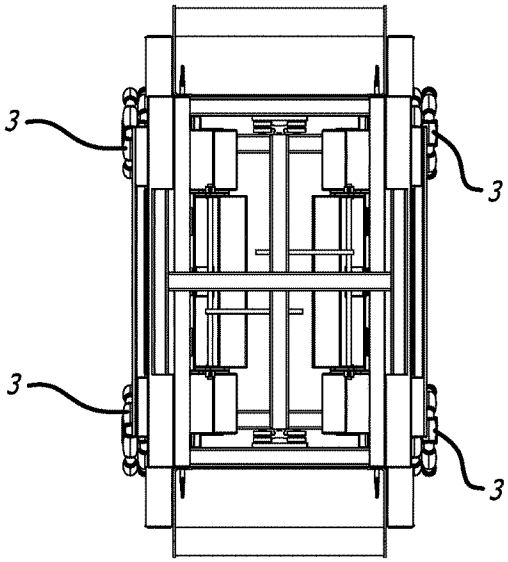
FIG. 19: Top view showing a Trolley with arms folded on the sides of the trolley body, and showing the vertical UVC lights and navigation wheels on the trolley.
Figure 18:
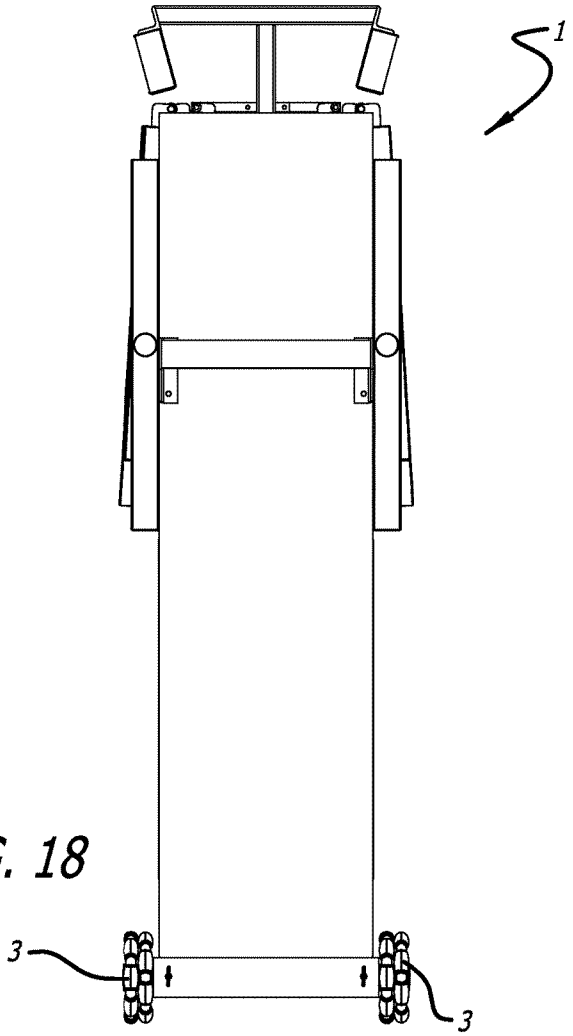
FIG. 18: Rear view showing a Trolley with arms folded on the sides of the trolley body, and showing the vertical UVC lights and navigation wheels on the trolley.
Figure 20:
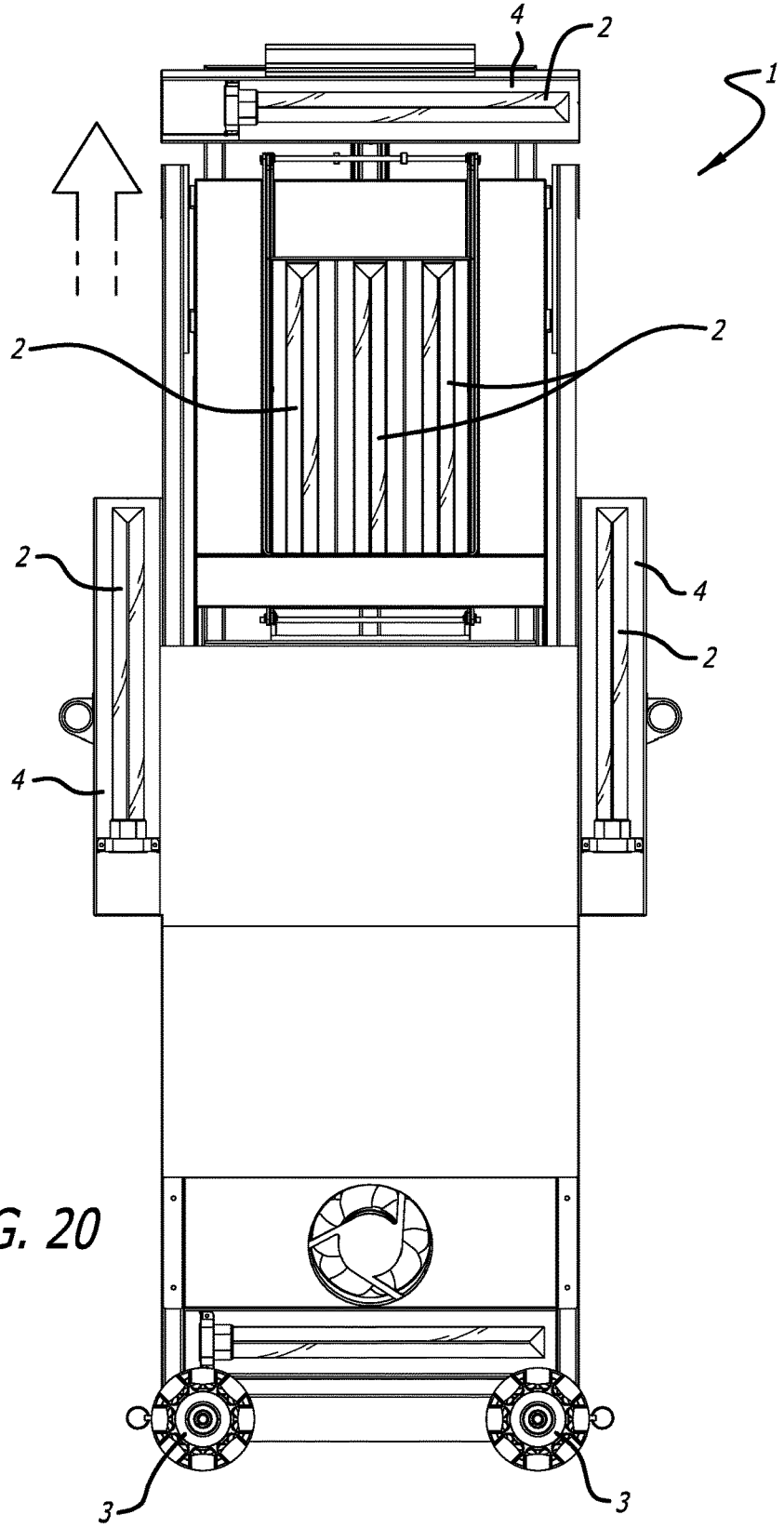
FIG. 20: Side view showing a Trolley with arms partly vertically extended and folded on the sides of the trolley body. Also there are vertically arranged fixedly mounted UV lamps mounted on the corners of the trolley and for directing the UVC light outwardly and transversely towards the area at the same height as the trolley and adjacent to the trolley. The navigation wheels on the trolley mounted on the outer perimeter of the body of the trolley.
Figure 21:
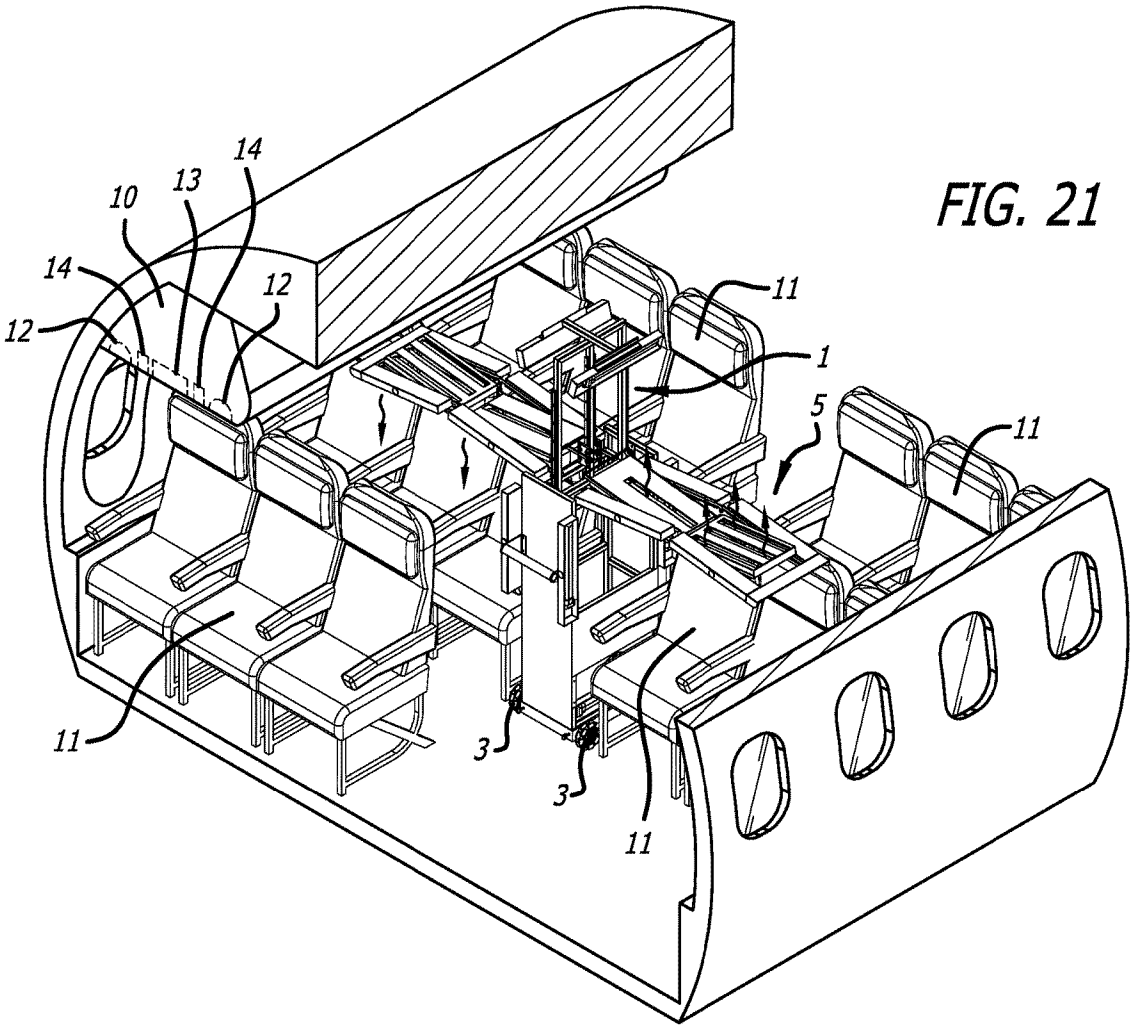
FIG. 21: Perspective view showing a Trolley in an aircraft aisle between rows of seats. The arms transversely extended over the seats and there are vertical support arms which are extended vertically from the trolley and have horizontally extended fixed UVC elements which project UVC light from a higher level above the trolley body trolley outwardly and transversely towards the area above the height of the trolley body.

Arms (5) may be configured in a variety of embodiments. FIGS. 1-4 show arms (5) essentially a folding frame containing UVC Sources (2) attached to a scissors like extension/retraction mechanism (6). The extension/retraction mechanism (6) may be attached to a linear actuator, not illustrated, and motor controlled by the microprocessor. FIGS. 5-8 show an alternative arm embodiment wherein the UVC Sources (2) are directly embedded within the extension/retraction mechanism (6). FIGS. 9-11 show a "roll-up" type arm embodiment with UVC sources (2) embedded into the extension/retraction mechanism (6). For clarity of illustration, these arms (5) contain a limited number of UVC sources (2). Many more UVC sources (2) may be desirable depending upon the desired dose of UVC exposure and other constraints.

These multiple embodiments are not intended to be all inclusive, but rather demonstrative of the myriad ways that this disclosure can be constructed.

Vertical extensions with laterally directed UVC sources (2) also expose the overhead bins. The height of these sources may vary, depending upon aircraft configuration.

Fans are also attached to the trolley (1) in such a manner to direct air flow into the path of UVC sources to sterilize the air. For example, fans directed laterally toward the floor can circulate air that might otherwise remain relatively stagnant. UVC light also generates ozone from ambient oxygen which helps deodorize the cabin as an additional benefit.

Rechargeable batteries are located within the trolley to power the motor, controller, navigation mechanism, fans, arm extension mechanism, sensors, other electronics, and UVC sources. Some UVC lamps may also require ballast. These heavier components are preferentially located at the lower portion of the trolley to maximize lateral anti-tip-over stability. A power cord port, not illustrated, allows plug in charging when the trolley is not in use. The batteries can be located within or attached to the trolley. In some forms, the batteries can snap on as an exterior battery pack, and the batteries can cooperate with a separate charging station. In this way, the robot can be used to sanitize several aircraft in succession by simply swapping the battery pack.

Operation

The trolley (1) is stowed off the aircraft, with arms (5) retracted, and plugged into an external power source to charge the on-board batteries. When ready for use, the apparatus of this disclosure is unplugged and wheeled onto the aircraft in a manner similar to known food/beverage trolleys. The trolley is positioned in the aisle between the first row (or last row) of seats. The trolley is autonomously centered by sensors and the navigation mechanism. Seats are detected by sensors or preprogrammed by the number of rows, for example. The arms (5) are extended utilizing the extension/retraction (6) mechanism. The UVC sources (2) are powered on with a delay mechanism sufficient to allow personnel to leave the aircraft, or remotely. The trolley (1) proceeds along the aisle, autonomously centered by the lateral proximity sensors and the wheel (3) navigation mechanism. The apparatus of this disclosure proceeds autonomously to the last row (or first row) of seats, detected by the aft proximity sensors or pre-programmed by the number of rows. The trolley (1) stops, reverses direction and proceeds in the opposite direction in the aisle to the starting point.

The trolley (1) speed of travel may be programmed and is dependent upon the UVC source output, distance from UVC source to surface, and desired level of kill rate. Kill rates are dose dependent, measured in Wsec/m2 and specific microbial sensitivities are known. The total treatment duration should conform to other ground turn-around time constraints for the aircraft.

When treatment is completed, the arms (5) are retracted to the stowed position. The apparatus of this disclosure is then transported back to the storage facility and plugged back into the external power source.

The device can be composed for instance, of three or more modules:

Cart—being the chassis, wheels, motors.

Base—which removably attaches to the Cart and is a covered frame. Attached are lamps with reflective housings and a telescoping mechanism. Electronics components fit within the Base (e.g. controllers/processors, ballasts). Battery pack(s) mount to the front and rear of the Base.

Wing Assembly—which fits into the Base with a telescoping mechanism that allows vertical translation as described below.

The three modules fit together and electrical connections are done via plug type connectors or wirelessly for signal transfer.

Advantages of this modularity include:

a) ease of manufacture b) ease of transport c) replacing a non-functional module rather than an entire unit.

Telescoping Wing Assembly

The Figures demonstrate the feature of the Wing Assembly that telescopes vertically into and out of the Base. This may be accomplished by a variety of known means including a track linear actuator, or a variety of gears, pulleys, chains, belts, etc.

Figure 22:
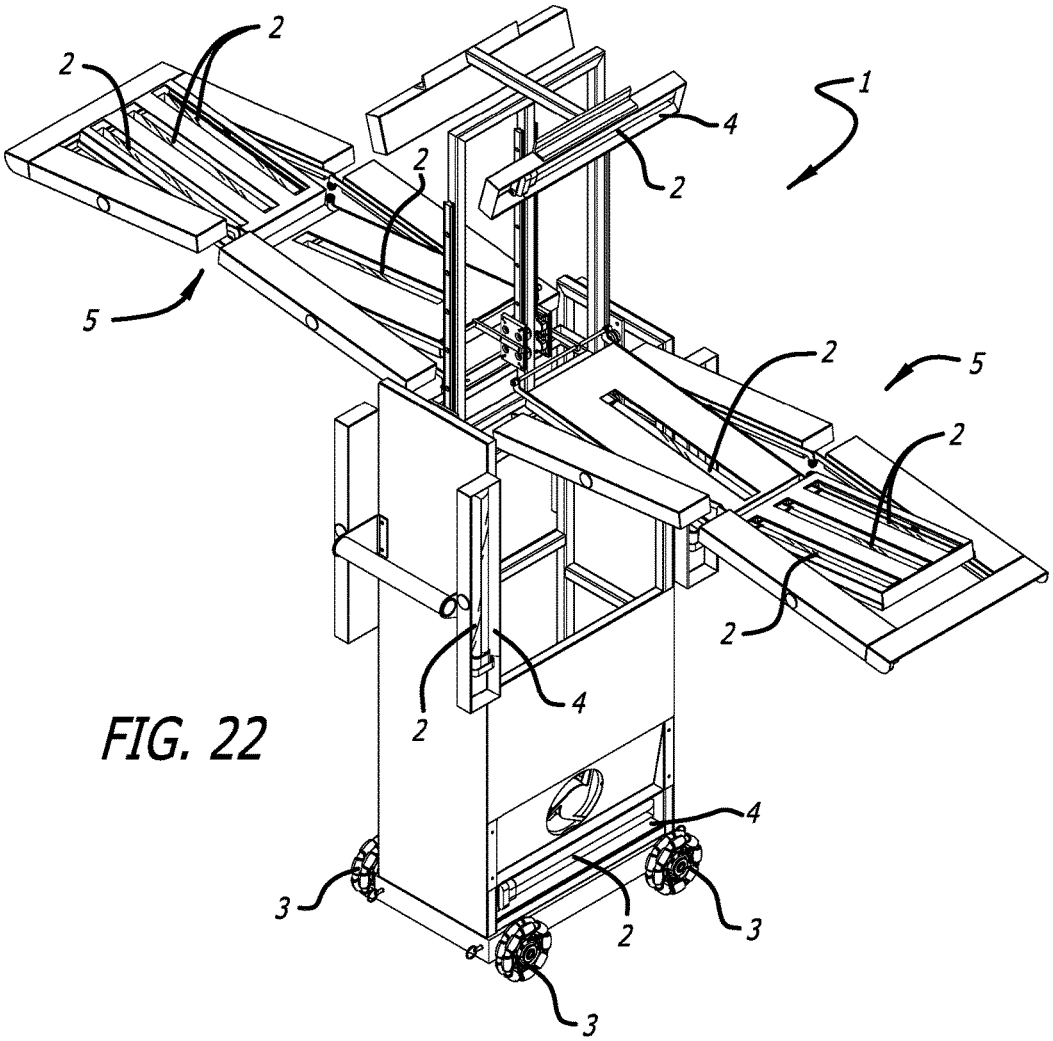
FIG. 22: Perspective detailed view showing a Trolley with arms transversely extended and vertical support arms which are extended vertically from the trolley and having horizontally extended fixed UVC elements which project UVC light from a higher level above the trolley body trolley outwardly and transversely towards the area above the height of the trolley body.
Figure 23:
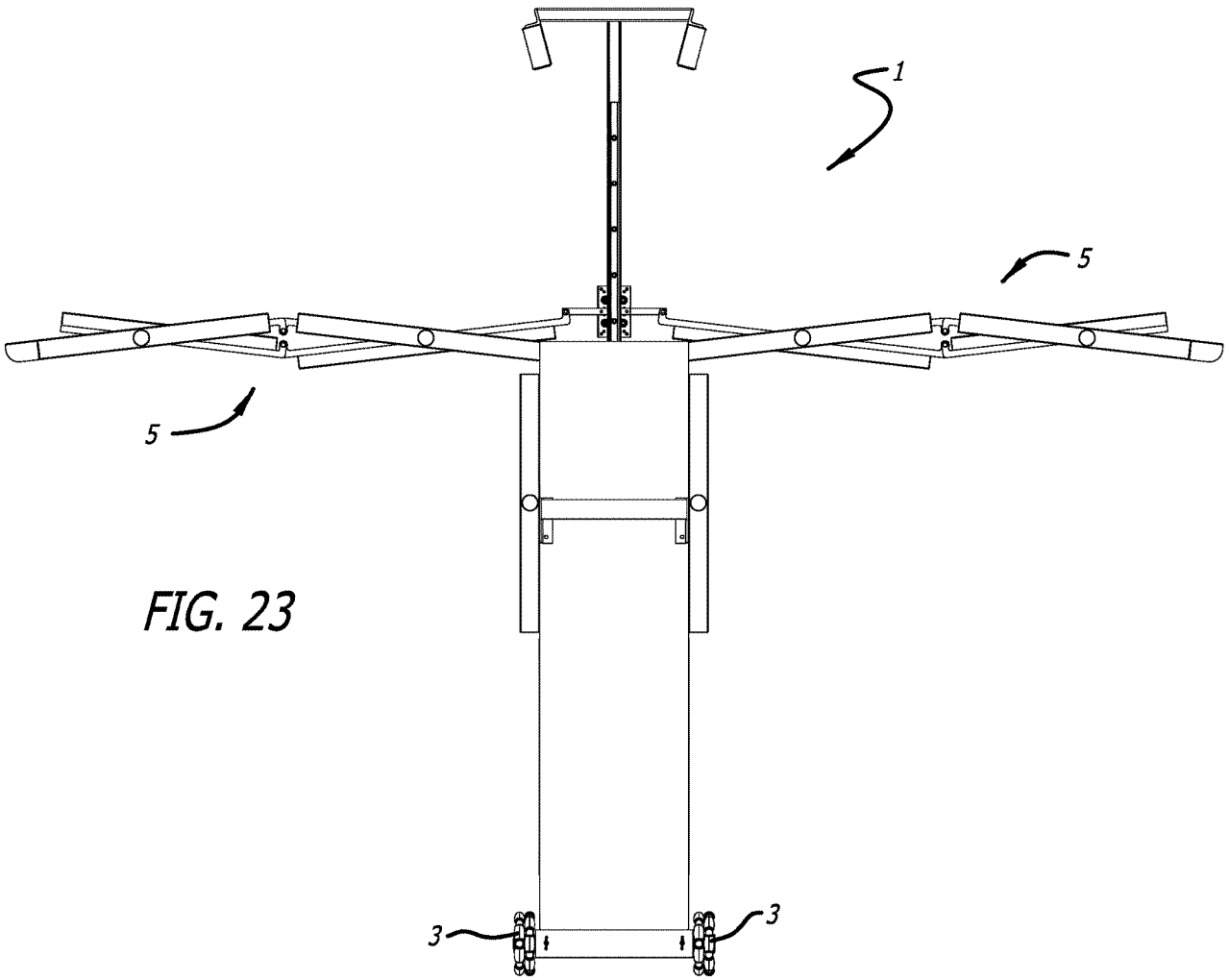
FIG. 23: Front detailed view showing a Trolley with arms transversely extended and vertical support arms which are extended vertically from the trolley and having horizontally extended fixed UVC elements which project UVC light from a higher level above the trolley body trolley outwardly and transversely towards the area above the height of the trolley body.
Figure 25:
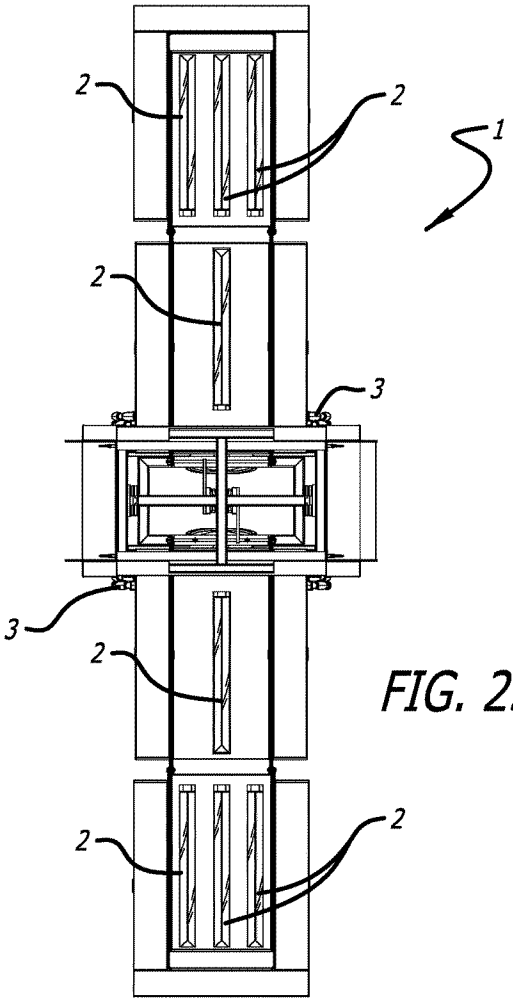
FIG. 25: Top detailed view showing a Trolley with arms transversely extended and vertical support arms which are extended vertically from the trolley and having horizontally extended fixed UVC elements which project UVC light from a higher level above the trolley body trolley outwardly and transversely towards the area above the height of the trolley body.
Figure 24:
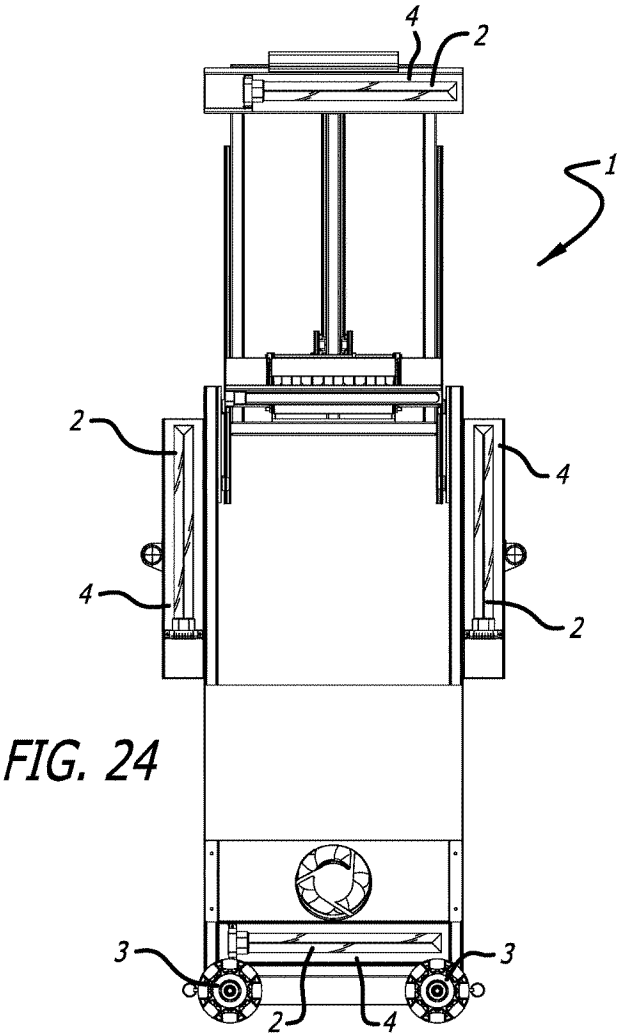
FIG. 24: Side detailed view showing a Trolley with arms transversely extended and vertical support arms which are extended vertically from the trolley and having horizontally extended fixed UVC elements which project UVC light from a higher level above the trolley body trolley outwardly and transversely towards the area above the height of the trolley body.
Figure 26:
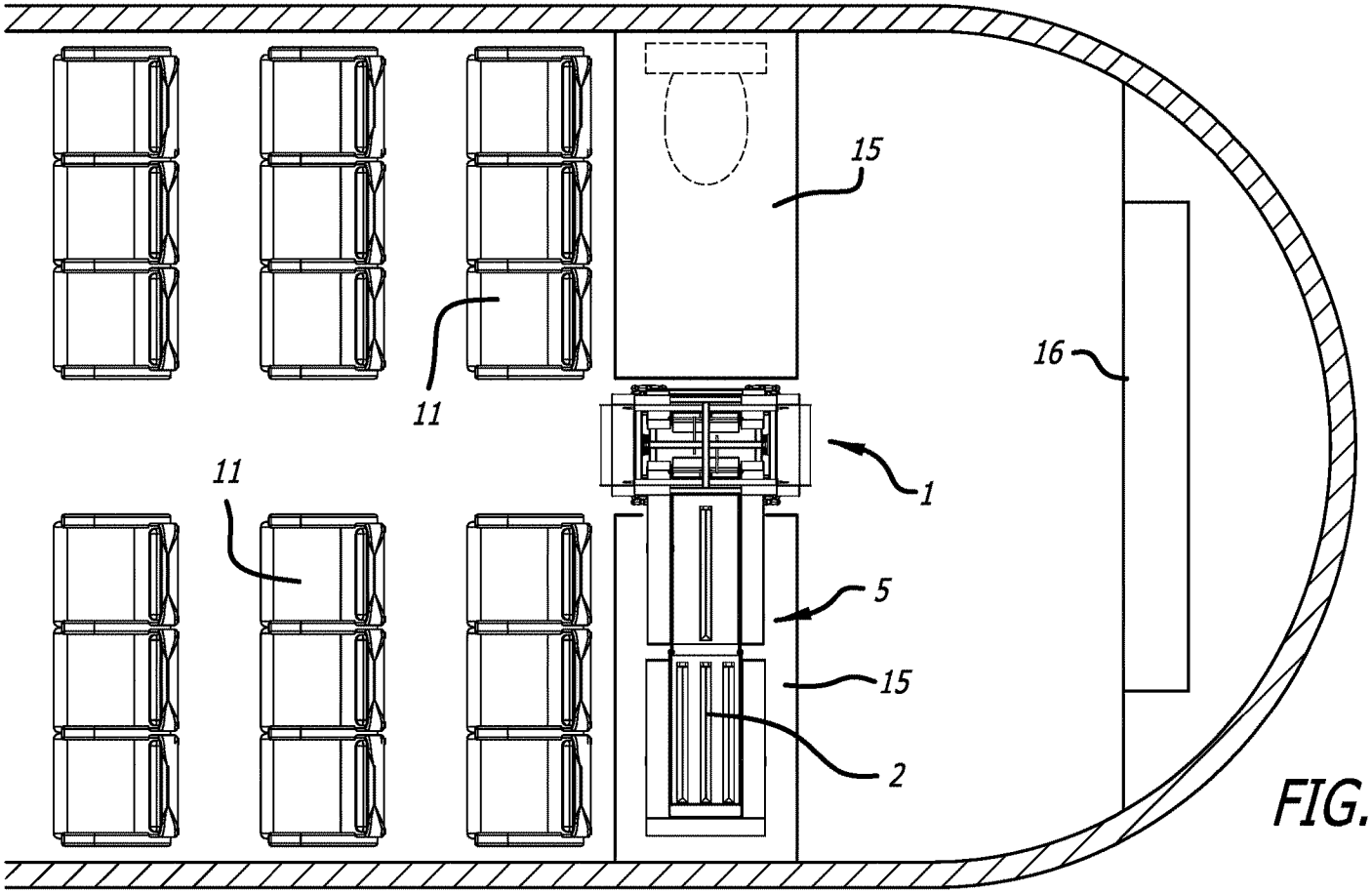
FIG. 26: Top view showing a Trolley an aircraft aisle having rows of seats, the trolley being adjacent the lavatory area behind or ahead of a row of seats. One set of the pair of arms transversely extends from the trolley body outwardly and transversely into the lavatory area of an aircraft.
Figure 27:
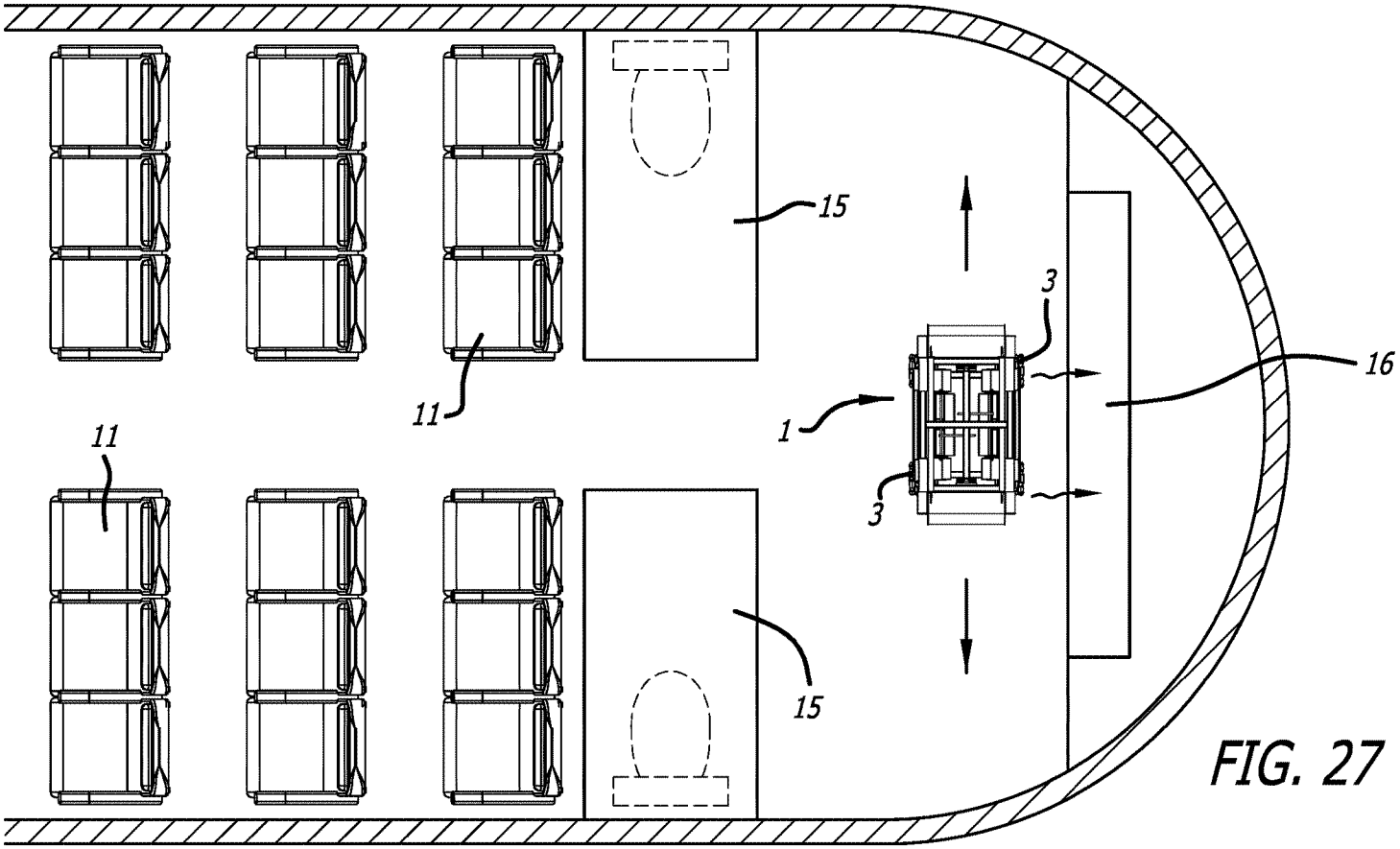
FIG. 27: Top view showing a Trolley an aircraft aisle having rows of seats, the trolley being adjacent the galley area behind or ahead of a row of seats. The pair of arms are folded in this view. The arrows indicate the extendibility transversely of the arms from the trolley body outwardly into the side areas of the galley area of an aircraft.
Figure 28:
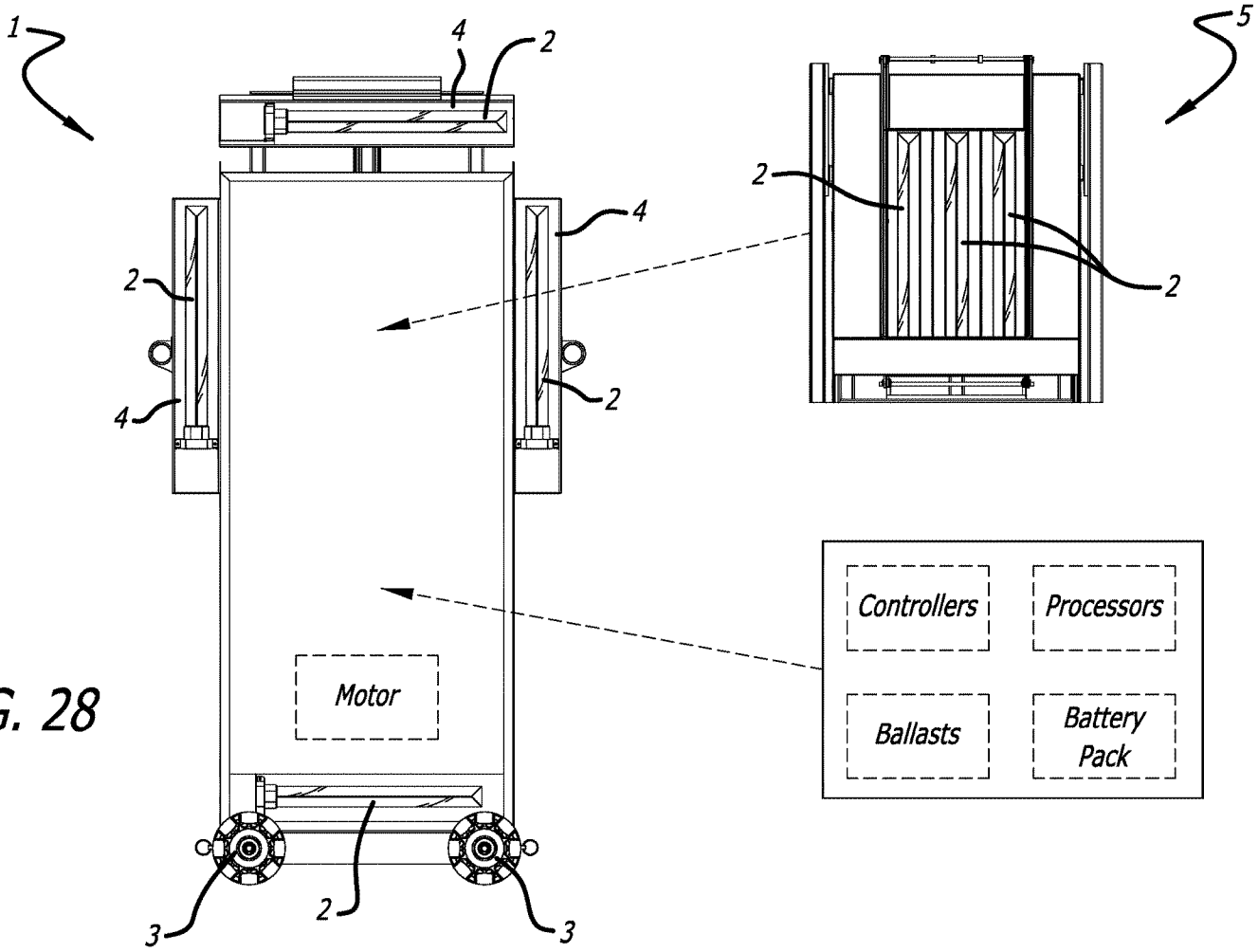
FIG. 28: Side view showing a Trolley with arms folded on the sides of the trolley body, and showing the vertical UVC lights and navigation wheels on the trolley, and the different modules of the Trolley, being the arms or wings as a first part or module; controller, processers, ballast and battery pack as second part modules, and the motorized body as third module or part. The trolley can be divided into less or more modules or parts.

Advantages of this telescoping feature include:

a. ease of access into shorter aircraft doorways b. markedly decreased tendency for tipping over c. facilitating modal operation described below d. accommodating a wider array of seating configurations Some Alternative Embodiments As shown in FIG. 22 there is a detailed view showing a Trolley with arms transversely extended and vertical support arms which are extended vertically from the trolley and having horizontally extended fixed UVC elements which project UVC light from a higher level above the trolley body trolley outwardly and transversely towards the area above the height of the trolley body.

The extended arms can be seen in the undulating type relationship, wherein the support perimeters around the lights are a hinged support with the lights extending between the perimeter supports. There are two sets or banks of UVC light sets for each arm, and there are at least one or two sets or banks of lights in side by side relationship such that there are at least three or four sets or banks of UVC lights on each arm. These lights extend light both downwardly and upwardly from the arm. In the extended relationship the perimeter supports pivot about a hinge so that supports are upwardly directed at the center hinge. With this extended relationship, the light banks are pivoted downwardly as the center about their central hinge.

Different Modes of Operation

Figure 29:
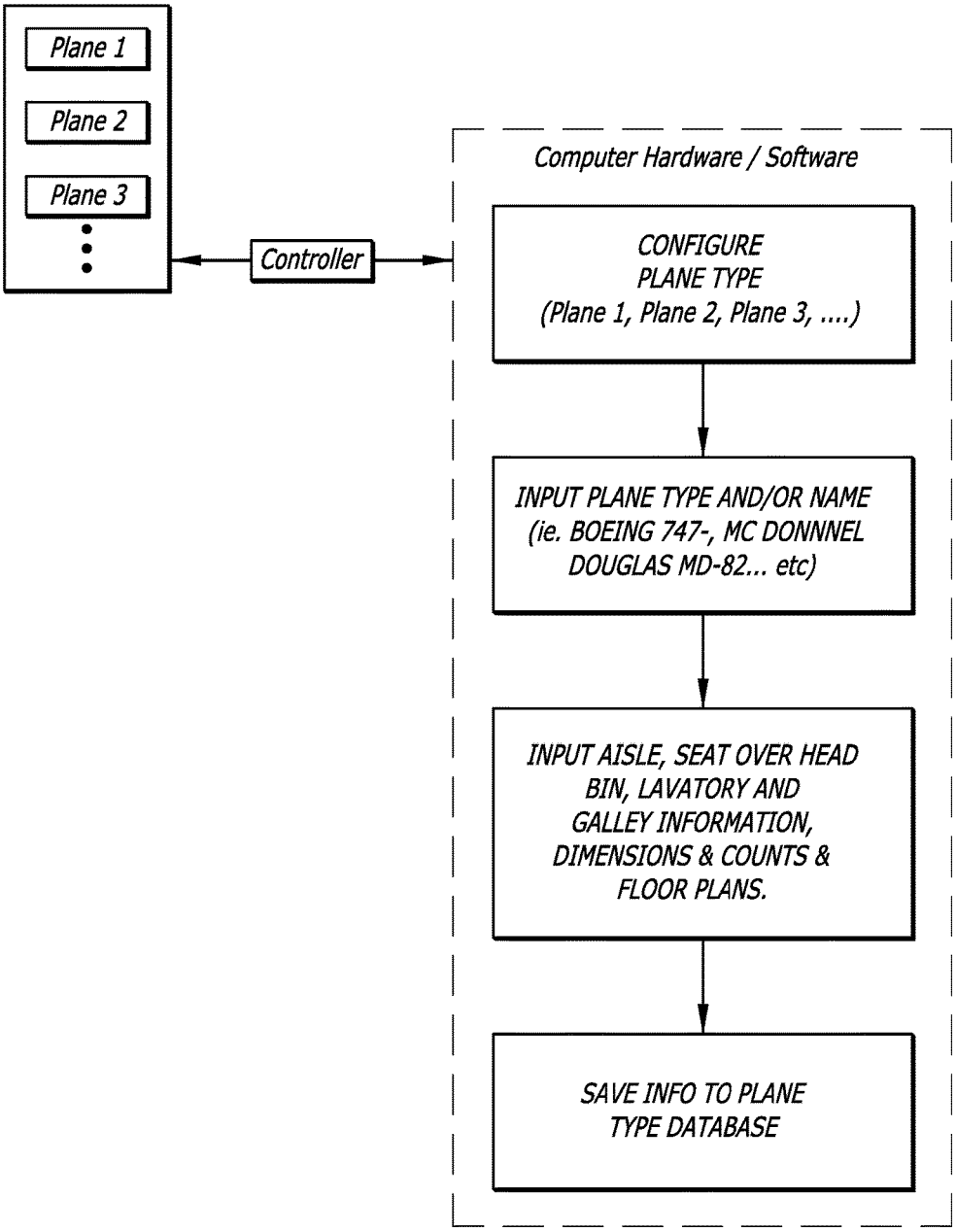
FIG. 29 is a first flow diagram illustrating the relationship of different planes and the controller device, and computer hardware and software for operation of the sanitizing device.

In addition to sanitizing the passenger seating area, which may be a primary source of germs, airlines and passengers are also concerned about contamination of the lavatory and galley areas. The device may feature "modes of operation", controlled via pre-programmed microprocessors, as indicated in the following table:

This is further illustrated and described with reference to FIGS. 29 to 31.

| MODE | LAMPS POWERED | WING DEPLOYMENT | WING ASSEMBLY POSITION | CART MOVEMENT |
|---|---|---|---|---|
| SEATING AREA | All | Both wings | Up to seatback height | Along aisle at pre-programmed rate of travel |
| LAVATORY | All Lamps on one side | One wing into lavatory | Primarily down toward toilet, but also actively moving upward to expose countertop, sink, etc. | Stationary for pre-programmed duration |
| GALLEY | Outer lamps on stowed wing and lamps on Base | Both stowed | Primarily down, but also actively upward to expose countertop and upper cabinets | Cart is turned 90 deg from aisle and moves across width of galley at pre-programmed rate |

The foregoing describes the minimum configuration of the current disclosure. A multitude of additions and variations are anticipated beyond this basic description. The following are representative examples of alternative embodiments and additional features, but are not intended to be all inclusive.

UVC sources may be fluorescent lamps, Light Emitting Diodes (LED), pulsed Xenon and other technologies known to produce ultraviolet light in the germicidal range.

The trolley has an estimated weight of approximately 75 pounds. A motor assist for pushing the trolley may be incorporated to ease in its mobility on and off the aircraft.

The UVC laden arms are foldable to substantially within the "footprint" of the trolley during transportation on and off the aircraft and for stowage. The arms extend substantially laterally and substantially perpendicular to the aisle at variable distance from the trolley. The two arms extend laterally independently to accommodate asymmetric seating configurations. There are a multitude of known mechanisms that allow this feature and some are illustrated within this application. More elaborate telescoping/folding/rolling or otherwise extensible mechanisms can be incorporated into the design and the disclosure includes such variations. The arms function independently of each other to optimally treat aircraft that may have different numbers of seats on each side of the aisle.

Because UVC light is potentially damaging to human skin and eyes, an onboard detection, warning and abort system is preferred. Sensors that monitor motion and heat or visual pattern recognition can be incorporated to detect human presence within a potentially dangerous radius of the device. Audible and visible alarms alert the human to the potential danger. The device stops and the UVC sources are depowered to prevent possible injury. Similarly cameras can be included to remotely monitor the trolley's progress. UVC does not penetrate clothing, plastics or glass and very simple personal protective gear covering all skin and a simple visor would allow a worker to be safely adjacent to the trolley.

Programming may involve varying levels of automation. For example, one may program for the cabin of a 777 aircraft and the controller determines the direction, speed, number of rows, the desired extension of the arms and height of the UVC sources for the overhead bins. Less sophisticated programming may have variable row numbers, seats per row, speed of trolley travel, depending upon level of contamination etc.

A more sophisticated travel path may also be anticipated and programmed. For example, the arms may be programmed to follow the contours of the passenger seat, going up and down around the seat backs and even down to the floor to bring the UVC sources into closer proximity to contaminated sources.

In the method, the device and apparatus is positioned to expose the UV source in a positioned to expose the components of the aircraft desired to be sanitized. There can also be a cleaning component with the apparatus and a waste container or tank with the device. The exposure of the cleaning component and the interior of the waste container or tank operates to control the proliferation of microorganisms and the generation of odor.

The extensible arms have the ability to disinfect surfaces that are not travelled over, but are remote from the travelled surface. Those surfaces, like seats, seat backs and tray tables cannot be travelled over and could not be sanitized are sanitized by the disclosed device which has those extensible arms.

An alternative embodiment could have the arms going up and down between seatbacks as the device travels in the aisle to get the arms closer to the sitting surface.

Surfaces like seats, seat backs and tray tables cannot be travelled over. Such surfaces could not be sanitized by a device that directs UV radiation to the surface on which it travels. The disclosed device, with extensible arms, allows such surfaces to be sanitized. The UV light also hits vent control surfaces in an aircraft cabin. While UVC is directed downward onto seats surfaces, a degree of UV is directed upward above the seats to sanitize the reading light (12), vent (13), and controls (14). This is to minimize the dispersion and existence of germs adherent to those surfaces. As seats, tray tables, armrests, etc. surfaces are traveled over with the wing extensions, as stated, analogously, air vents, light controls, attendant call buttons are traversed from underneath as the robot travels with these wing extensions.

An alternative embodiment could have the arms going up and down between seatbacks as the device travels in the aisle to get the arms closer to the seat surfaces.

An alternative embodiment is a permanent installation onboard an aircraft with a storage compartment. There can be a configuration of the disclosure where the device would be stowed in a closed compartment and rather than wheels, for example a ceiling mounted rail system allows the device to travel fore and aft in the passenger compartment. An advantage to this system is that the aircraft can be sanitized regardless of whether the airport has functioning devices. A further advantage is apparent in case of an on-board inflight release of a pathogen, whether accidental/unintentional or bioterrorism. By activating an onboard device, with passengers shielded, an aircraft can be "sanitized" inflight prior to landing. This would avoid release of potential pathogens at the destination and neutralize the threat prior to human inoculation.

Intelligence/Programming for Seating Configuration

The device has a programmable microcontroller/processor that receives information from the user and a multitude of on-board sensors. This component controls the lamp power, wing deployment, and wing-assembly telescope position and cart position/movement.

There are dozens of seating and cabin configurations in use with additional configurations added annually. These include variations in: aisle widths, bends, floor surfaces; Seat widths, heights, reclinability, surfaces, row spacing; overhead bin and vent/light controls; lavatory numbers, locations, fixture placements; galley locations, countertop heights, and inserts.

Once an airliner's interior is configured, the device can be programmed specific to that configuration and can be made to read the plane's tail number and know the configuration. Programs for different known aircraft configurations and for new aircraft configurations are implemented with the device and method of usage of the device. These programs are tied to a sanitization device and a particular airplane. These programs transform a particular article into an airplane from un-sanitized to a sanitized and germ cleaned device, namely from a viable germ environment, area or surface to a dead germ environment, area or surface.

A method and system of sanitizing seat surfaces in a location related to a public mass transportation vehicle includes a passenger area at the location. The area has multiple rows of seats arranged opposite to each other with an aisle between the opposite rows. There are the steps of:

a) providing a sanitization device including a mobile body configured to travel along the aisle of the passenger area of the vehicle;
b) extending the sanitization device laterally from the mobile body across a seat surface, a source of UV radiation being mounted on the sanitization device;
c) moving the sanitization device across a first seat surface;
d) exposing the first seat surface to UV radiation produced by the source;
e) moving the mobile body along the aisle while the device moves over seats surfaces of subsequent seat rows;
f) directing a source of UV radiation to the seat surfaces at a predetermined dosage while the device moves over seats surfaces; the mobile body being powered by a power source on board the mobile device;
g) programming a programmable microcontroller/processor for receiving information from a user and a multitude of sensors on the sanitizing device, the sensors being for accessing and determining the relative location of the device in the environment for sanitizing; and
h) having the processor control at least one of the radiation power, the lateral deployment of the sanitizing device, a vertical telescoping position of the sanitizing device and the device position and movement device in the environment for sanitizing.

The method and system is for sanitizing one of a designated aircraft. The aircraft has an aisle width, a bend, a floor surface plan, a seat width, a seat height, seat reclinability, seat surface character, seat row spacing, overhead bin and vent/light control, lavatory number, lavatory location, fixture placement, galley location, countertop height. A map of the aircraft is provided. The computer program inputs for application to operate the sanitizing device at least one characteristic of the map being an aisle width, a bend, a floor surface plan, seat width, seat height, seat reclinability, seat surface character, seat row spacing, overhead bin and vent/light control, lavatory number, lavatory locations, fixture placement, galley location, countertop height. This provides a sanitizing device programmed to sanitize the designated aircraft.

The method and system can be for sanitizing one of a designated aircraft. The aircraft has a designated plane tail number, and has the tail number relate to a configuration of the plane including providing a map of the aircraft. The device can be programmed specific to the configuration and reading the plane tail number to thereby apply the configuration to an operational program of the sanitization device.

Figure 30:
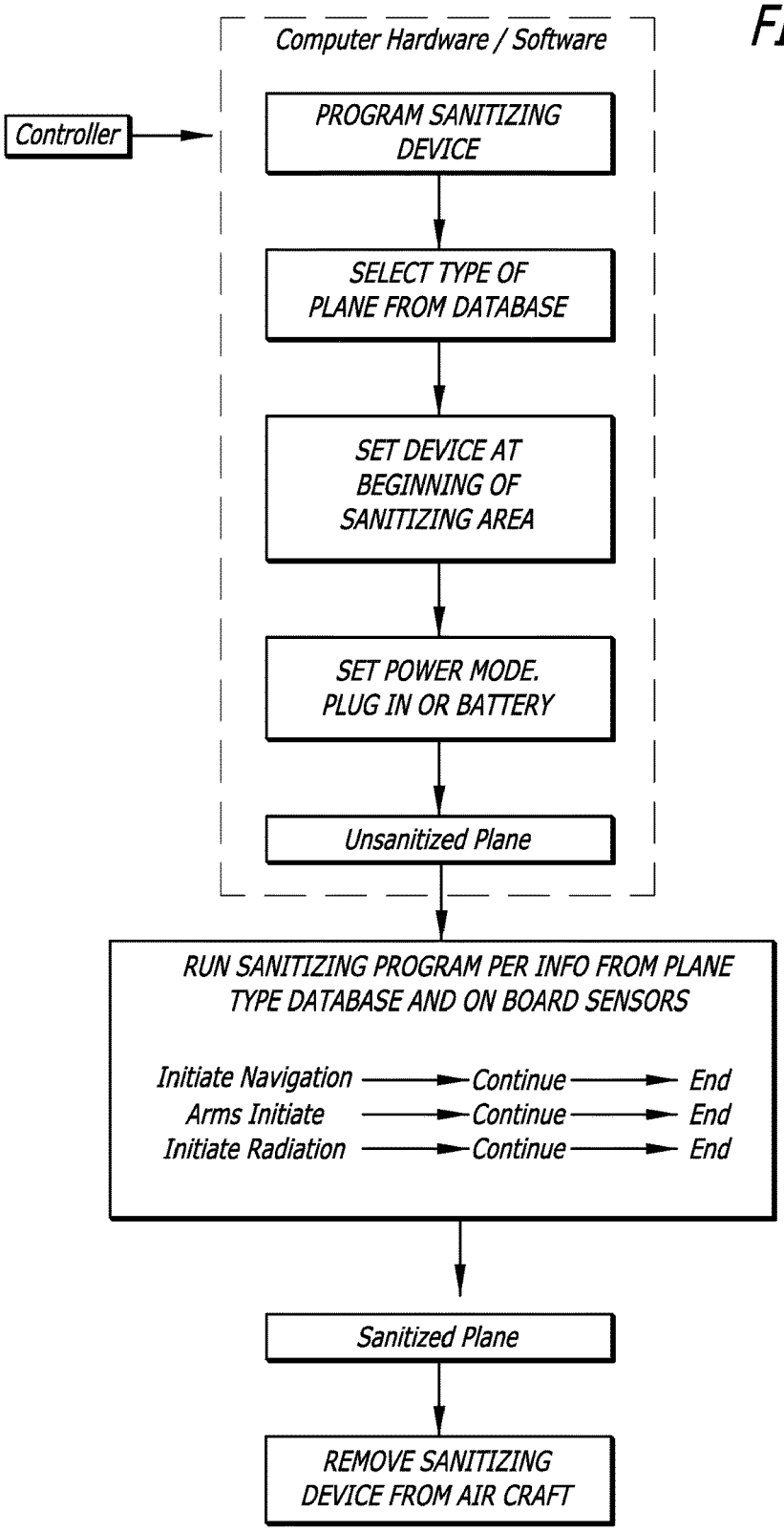
FIG. 30 is a second flow diagram illustrating the relationship of the controller device, computer hardware and software for operation of the sanitizing device, and the unsanitized pane and the sanitized plane.
Figure 31:
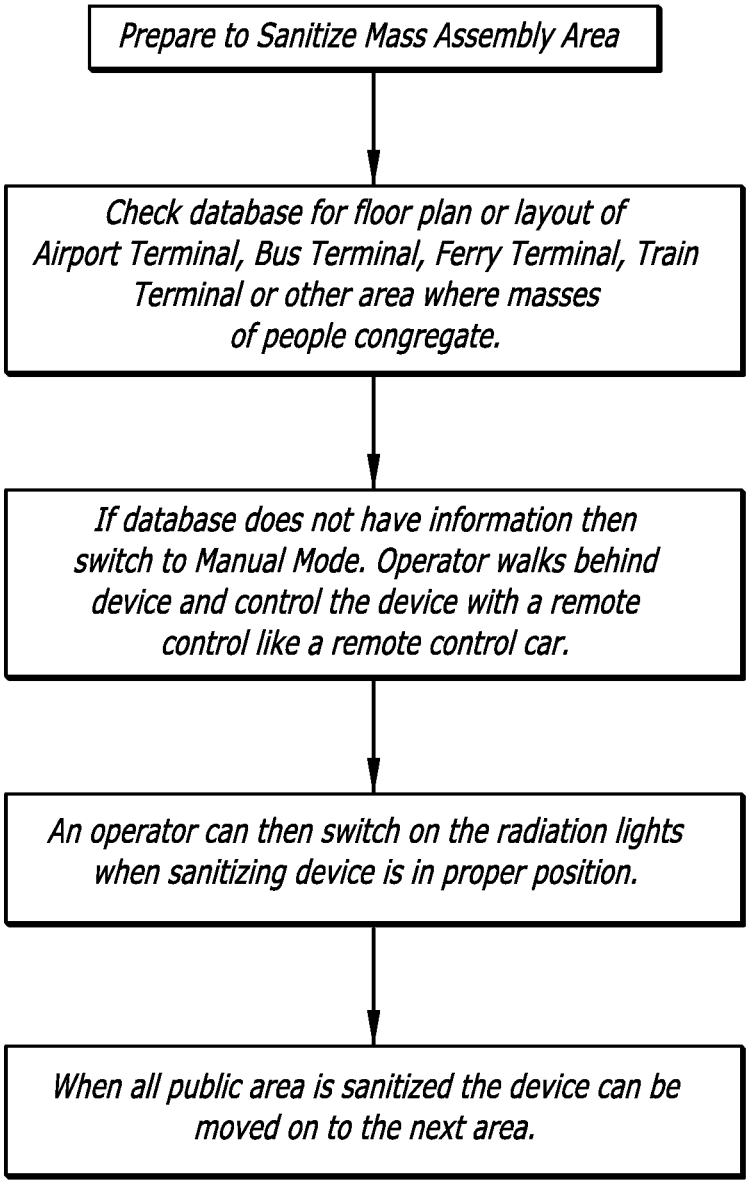
FIG. 31 is a flow diagram illustrating the relationship of different areas of mass assembly for operation of the sanitizing device.

As shown in FIGS. 30 and 31 there is shown the method and system for a controller reading and accessing different planes: namely plane1, plane2 and plane3. With the selected plane1, plane2 or plane3, the controller then configures the hardware and software of different features of the kind of plane including the different details of the floor map and features of the seats and other plane map. This plane data is saved into the database relating to the plane and the sanitizing device.

The controller then operates the computer hardware and software to program the sanitizing device, being selection of the type of plane, setting the device to operate, powering sanitizing device, beginning sanitizing, continuing sanitizing, ending sanitizing and finally obtaining a sanitized plane. At this time the device is removed from the aircraft.

Figure 32:
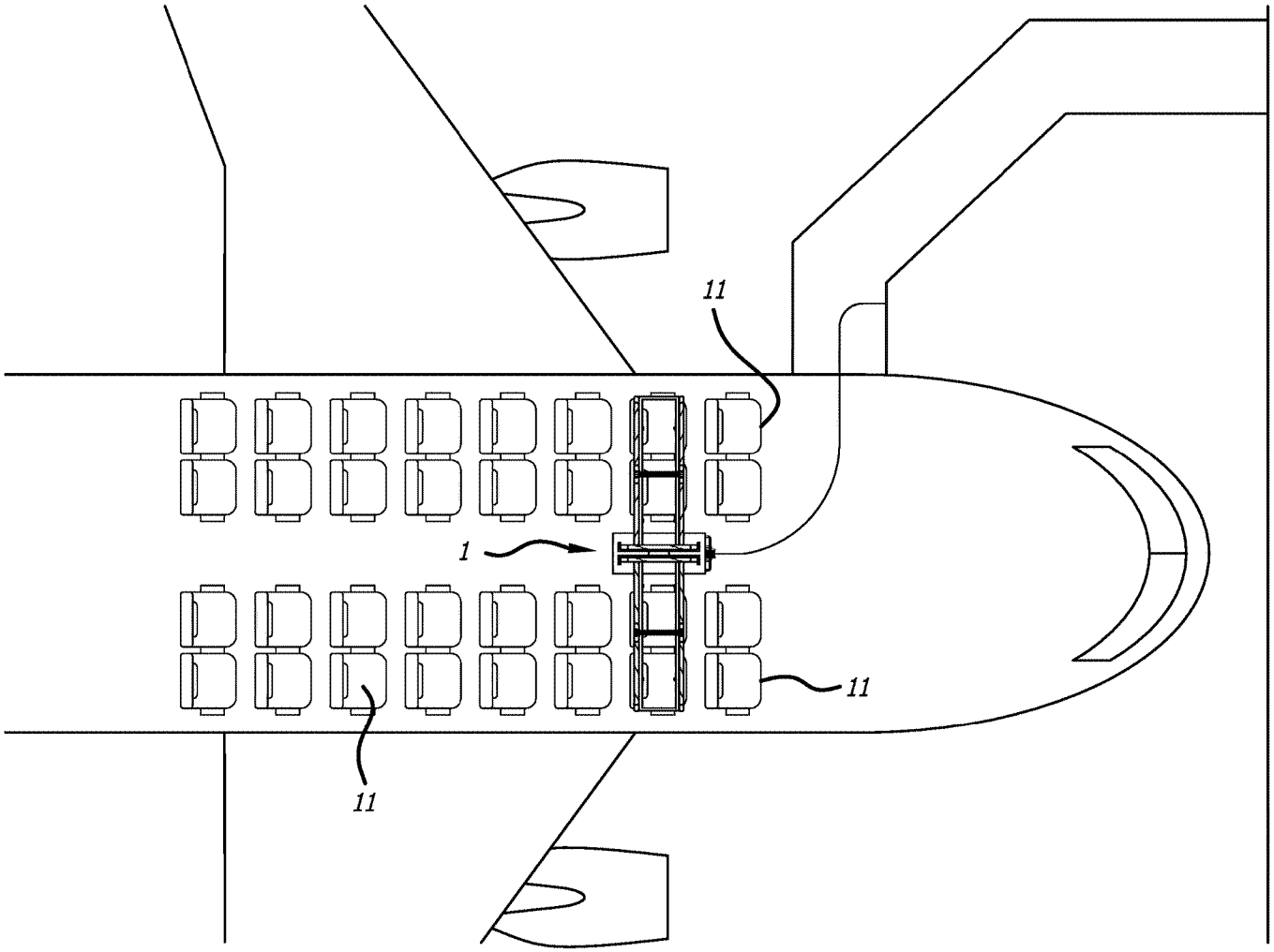
FIG. 32 Top view showing a trolley, an aircraft aisle having rows of seats, the trolley being between and adjacent the seats. The pair of arms are extended in this view. The device is connected by an electrical for power from a gangway electrical outlet.
Figure 33:
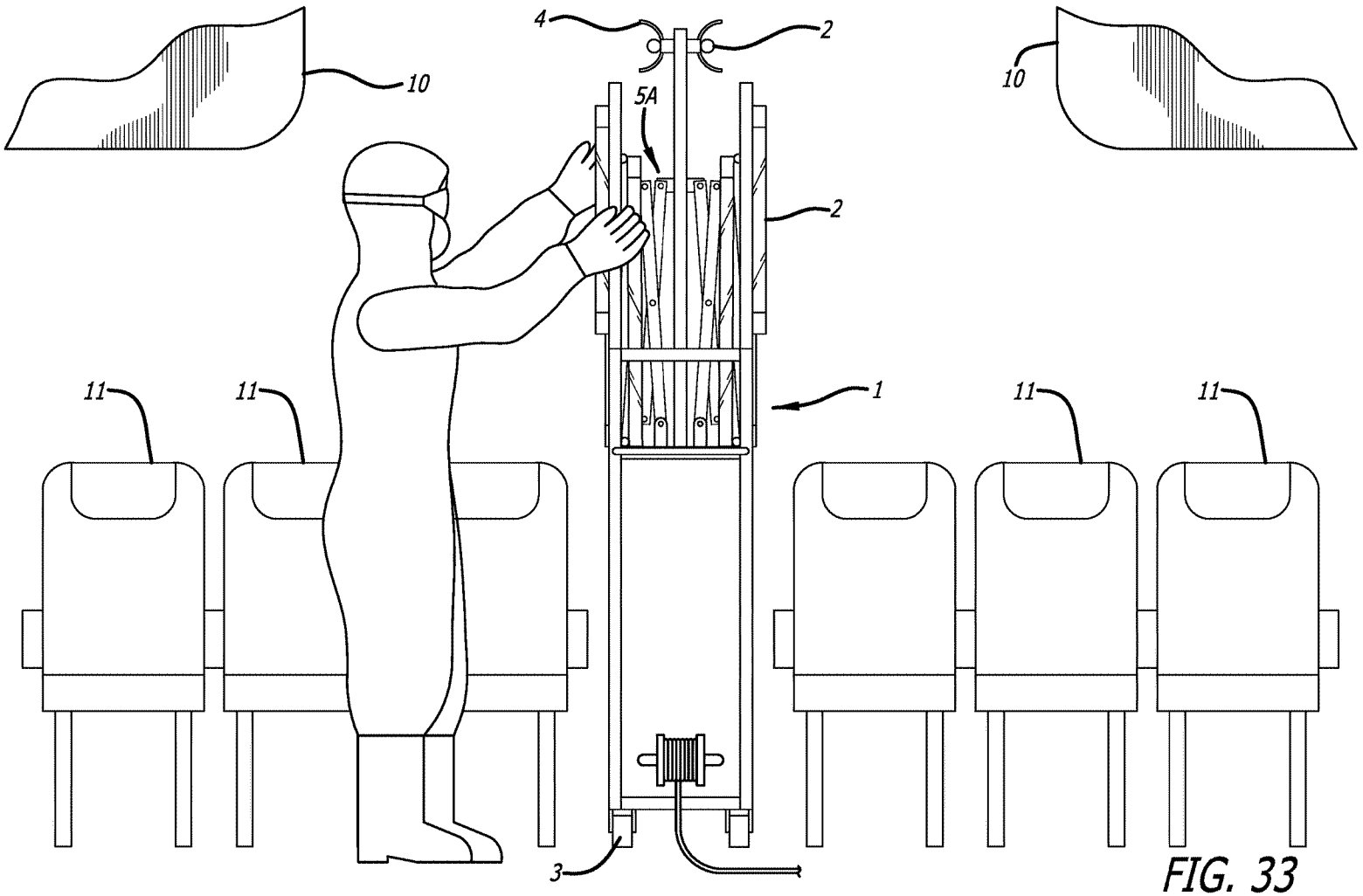
FIG. 33: Front View of Trolley with Arms in Stowed/Retracted Positions and an operator suited up for protection against UV light. There is a power cable reel shown at the bottom of the trolley with the electrical power line extending from the reel.
Figure 34:
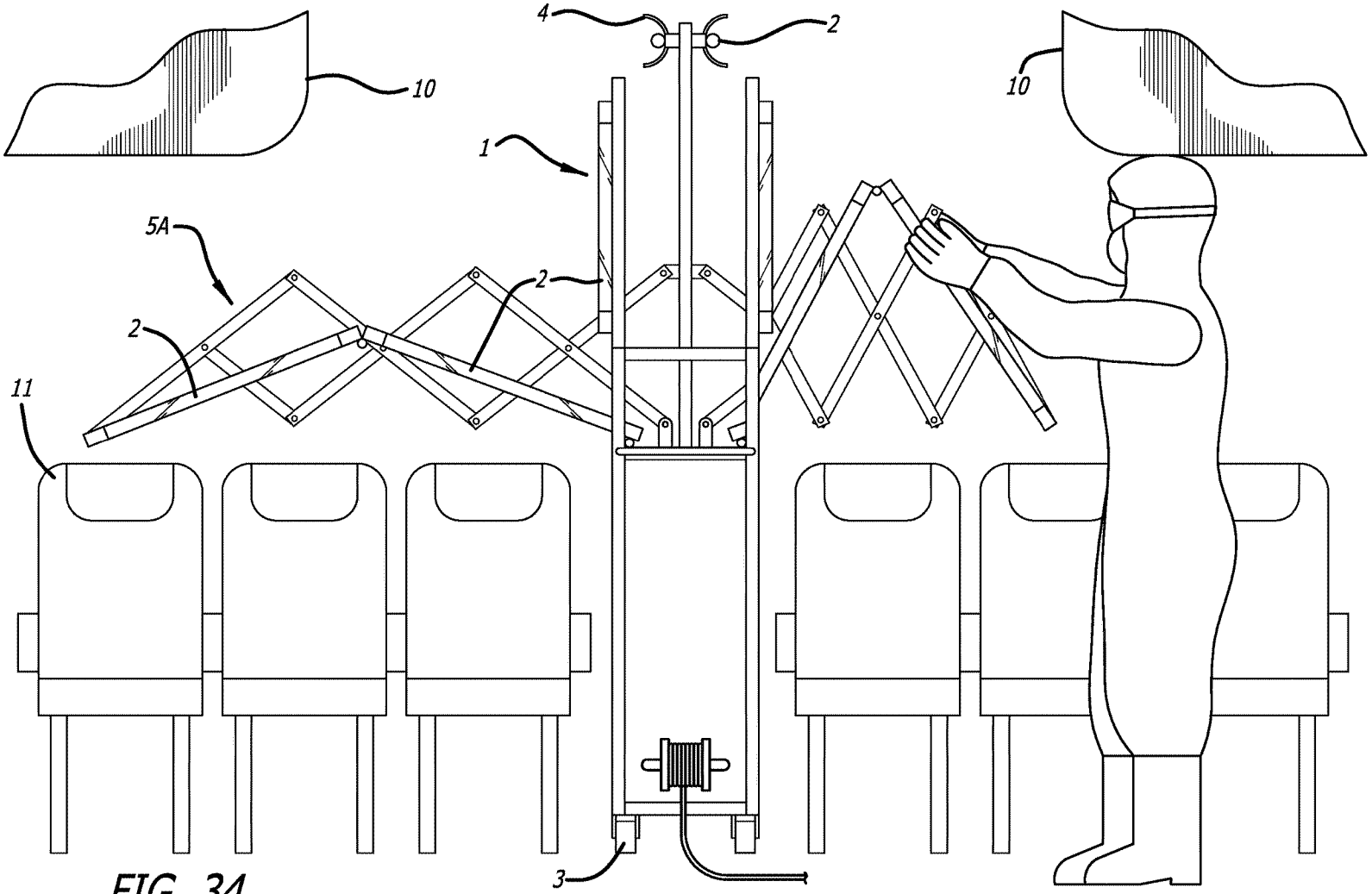
FIG. 34: Front View of Trolley with Arms in extended and being manipulated by an operator suited up for protection against UV light.
Figure 35A:
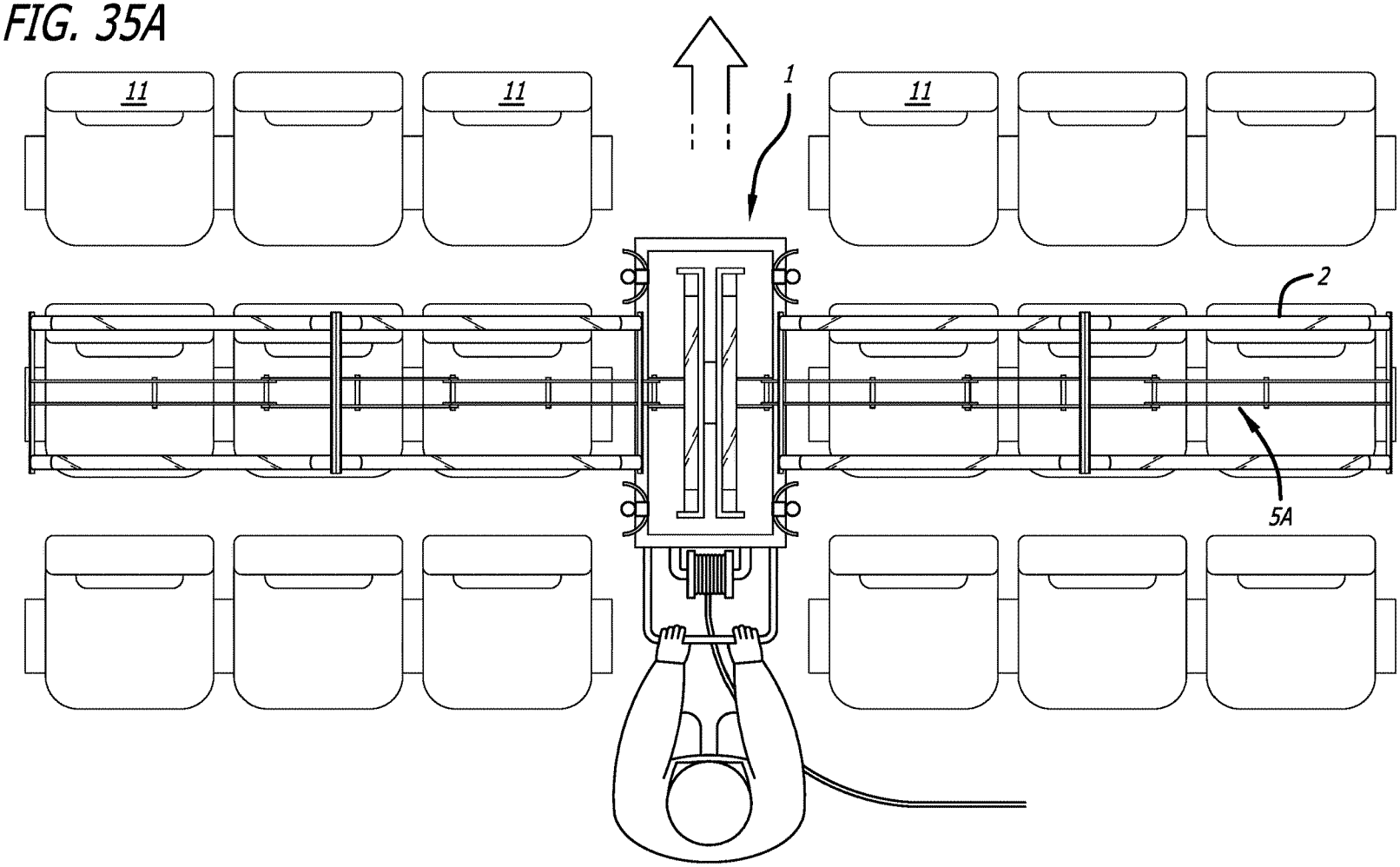
FIG. 35A: Front View of Trolley with Arms extended and the trolley being driven down the aisle by an operator suited up for protection against UV light.
Figure 35B:
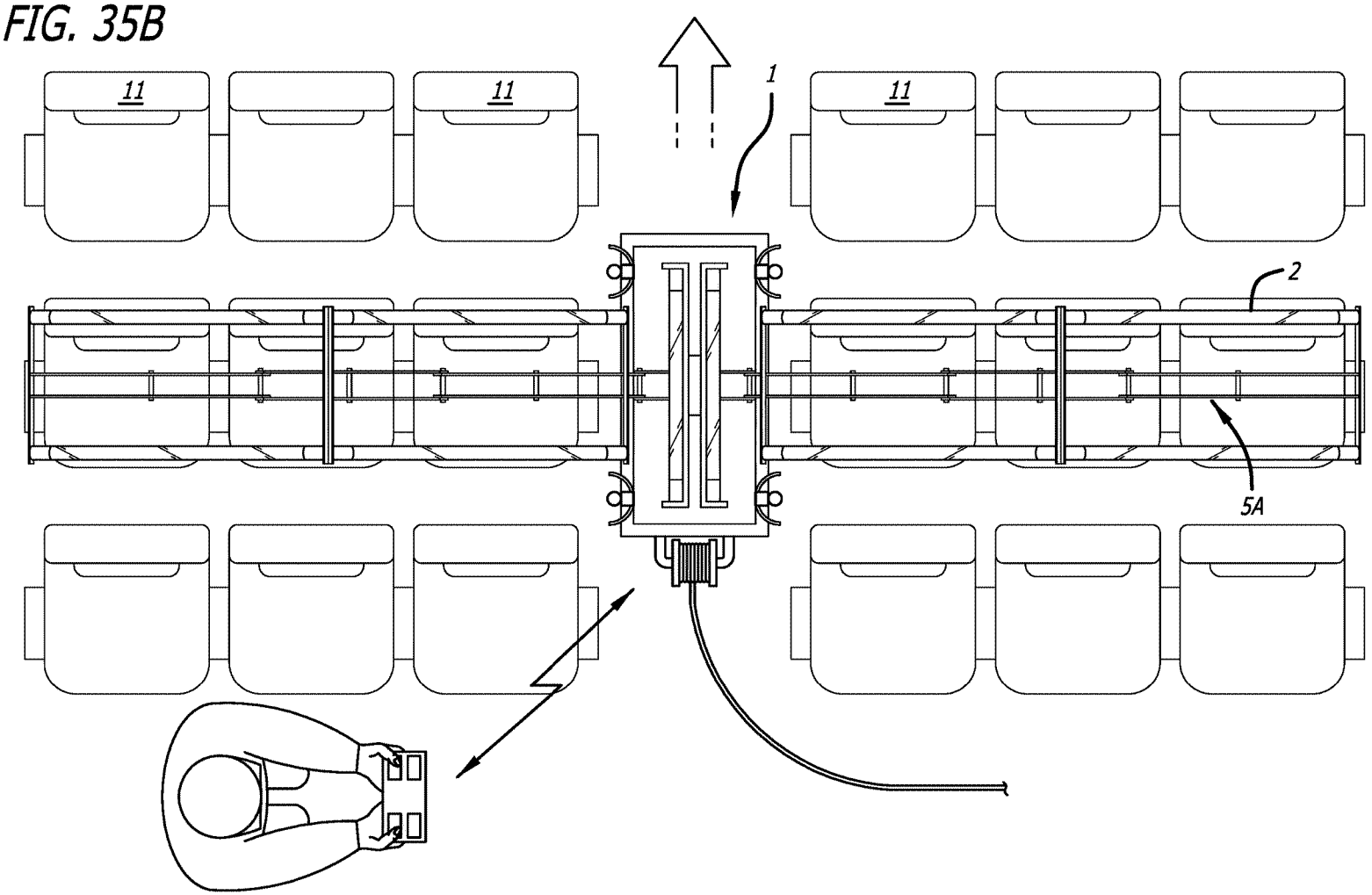
FIG. 35B: Front View of Trolley with Arms extended and the trolley being driven down the aisle by a remote control operated by an operator suited up for protection against UV light.
Figure 36:
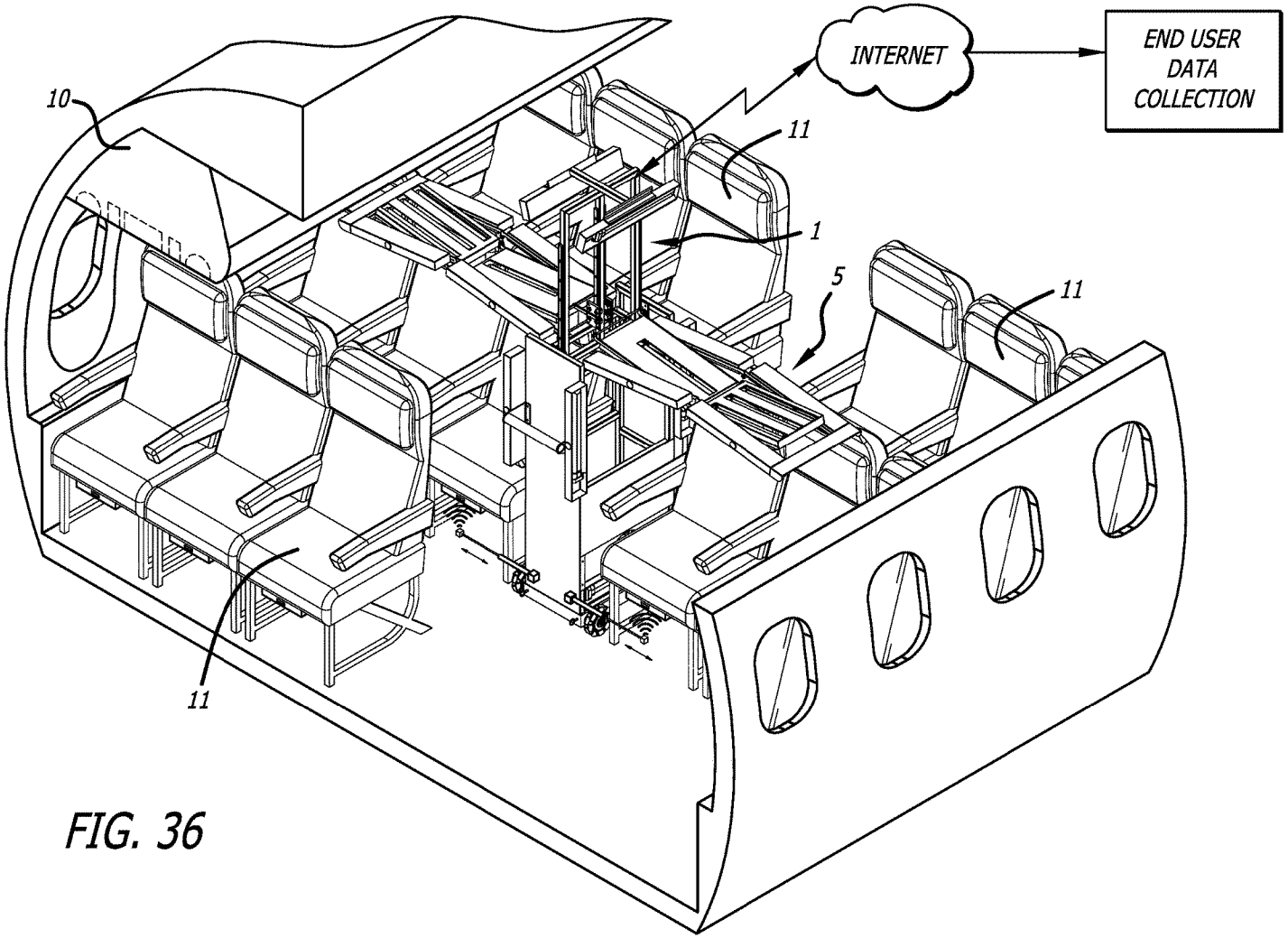
FIG. 36. Perspective view showing a Trolley with arms extended in an aircraft aisle between rows of seats, and with sensors at the bottom of the trolley probing the areas under the seats, for instance life jackets with RF tags, and with a transmitter for communicating through the internet to an end user for data collection. The sensors on the trolley can be placed at different strategic locations on the trolley and be for different purposes including sniffing for dangerous chemicals and devices.

When used in a mass assembly area where there assemblies of people, the system can operate similarly and be programmed in the same manner. In alternative form, there is a database check of the floor plan, and if there is not stored data about the floor plan the system is operated mainly by an operator who walks behind or with the device and controls the device in manner similar to controlling a remote control car. This is illustrated in FIG. 32.

In some other forms of the disclosure the sanitizing device can drive autonomously in and about the mass assembly areas such as an aisle of a plane, a waiting area or room. In this manner the device is fitted with sensors for effecting navigation of the device over an area in a way similar to the navigation of a driverless car.

Different Power Alternatives

The sanitizing device and method is compatible with either battery power or mains power. There can be a detachable battery pack and inverter that attaches to the device and accommodates the 115 v plug. Alternatively, there can be a connector plug for plugged into a 115 v extension cord.

There are different applications of the method and system for sanitizing areas and surfaces. The method and system is for use on locations being related to public mass transportation vehicles. As such, this can be used on buses, trains, ships, boats, ferries and waiting rooms and areas where passengers normally sit.

The system and method applies to areas of mass assembly or association or congregation of people, public assembly areas and venues where there are attendees.

Robots of the system and method sanitize theatres (live or movie), sports arenas and venues of public assembly. Although this disclosure refers primarily to aircraft, the technology is applicable to all forms of mass transit and public areas as described. Such mass assembly areas could be selectively a mass transportation vehicle, a passenger area at the location, or a venue for entertainment or sport.

Further although the disclosure relates to UV lighting, there can be other forms of lighting or radiation which are used which effectively sanitize areas by applying the appropriate wavelengths and power levels. Further instead of the tubular format of dispersing the light there can other geometric and/or compact shapes of lighting source which are used, and for instance these could include appropriate LED lighting formats.

Many different formats are possible for the disclosure. It is therefore to be understood that within the scope of the appended claims the disclosure may be practiced otherwise than as specifically described.

What is claimed is:

1. A method of sanitizing seat surfaces in an area, the area having multiple rows of seats arranged opposite to each other comprising the steps of: a) providing a sanitization device including a mobile body configured to travel along the area; b) extending a portion of the sanitization device laterally from the mobile body across a seat surface, a source of germicidal UV-C radiation being mounted on the portion of the sanitization device; c) moving the portion of the sanitization device across a first seat surface; d) exposing the first seat surface to germicidal UV-C radiation produced by the source at a predetermined dosage; e) moving the mobile body along the area while the portion of the sanitation device moves over other seat surfaces of subsequent seat rows; and f) directing the source of germicidal UV-C radiation to the other seat surfaces at the predetermined dosage while the device moves the portion of the sanitization device laterally over the other seat surfaces; the mobile body being powered by a power source on board the mobile device, providing an additional power source for the mobile body being provided from an outlet remote from the mobile body, the mobile body being selectively set up for being manually operated and driven by an operator, the operator selectively being protected with skin and eye protective gear, providing the UV-C radiation by multiple UV-C lamps in two laterally opposite directions each respectively by two laterally extendable portions relative to the movable body, the UV-C radiation being provided by the multiple spaced apart UV-C lamps on each portion in each of the lateral directions while the mobile body moves and while the portions extend laterally outwardly from the body, and wherein the portions are extendable from the mobile body between different lateral extendible positions and are movable over multiple seats and the multiple UV-C lamps are directed to the surfaces of the multiple seats such that the multiple UV-C lamps are set up to be extendable over the multiple seats, and wherein the UV-C lamps are movable inwardly towards the device and outwardly from the device to extend laterally between the different lateral positions over the multiple seats, and wherein the portions are laterally extendable from the mobile body by movement from a position within the body to the different positions out of the body.

2. The method of claim 1 including a remote control for permitting the operator to control the device while remotely located from the device.

3. The method of claim 1 wherein the public area is a movie theater, theater, sports arena, arena, entertainment arena, or waiting room.

4. The method of claim 2 wherein the public area is a movie theater, theater, sports arena, arena, entertainment arena, or waiting room.

5. A method as claimed in claim 1 wherein the seat surfaces are in an aircraft passenger cabin, the cabin having multiple rows of seats arranged opposite to each other with an aisle between the opposite rows; and wherein the mobile body is composed of at least two separable components.

6. The method of claim 5 including a remote control for permitting the operator to control the device while remotely located from the device.

7. A method of sanitizing seat surfaces in an area, the area having multiple rows of seats arranged opposite to each other with an aisle between the opposite rows comprising the steps of: a) providing a sanitization device including a mobile body configured to travel along the aisle of the area; b) extending two arms of the sanitization device laterally in opposite directions from the mobile body across a seat surface, multiple sources of germicidal UV-C radiation on each arm being mounted on the arms of the sanitization device; c) moving the arms of the sanitization device across a first seat surface; d) exposing the first seat surface to germicidal UV-C radiation produced by the multiple sources at a predetermined dosage; e) moving the mobile body along the aisle while the portion of the sanitation device moves over other seat surfaces of subsequent seat rows; and f) directing the sources of germicidal UV-C radiation to the other seat surfaces at the predetermined dosage while the device moves the portion of the sanitization device laterally over the other seat surfaces; providing the UV-C radiation by multiple UV-C lamps on each of the two arms thereby to be in two laterally opposite directions relative to the mobile body, each being respectively by two laterally extendable arms relative to the movable body, the UV-C radiation being provided by the multiple spaced apart UV-C lamps on each arm in each of the lateral directions while the mobile body moves and while the arms extend laterally outwardly from the body, and wherein the arms are extendable from the mobile body between different lateral extendible positions and are movable over multiple seats and the multiple UV-C lamps are directed to the surfaces of the multiple seats such that the multiple UV-C lamps are set up to be extendable over the multiple seats, and wherein the UV-C lamps are movable inwardly towards the body and outwardly from the body to extend laterally between the different lateral positions over the multiple seats, and wherein the arms are laterally extendable from the mobile body by movement from a position within the body to the different positions out of the body.

8. The method of claim 7 wherein the arms are for independent operation.

9. The method of claim 7 including controlling the motion of the arms over and about aircraft surfaces, such surfaces including seats of an aircraft.

10. The method of claim 7 wherein the arms are mounted with the mobile body and extendable from the mobile body at a position above back rests of the seats, and are movable over the seats and the UV-C lamps are directed to the seat surfaces.

11. The method of claim 7 wherein the arms are mounted with the mobile body and extendable from the mobile body at a position essentially solely above seats of an aircraft, and is movable over the seats and the UV-C lamps are directed to the seat surfaces.

12. The method of claim 7 wherein the respective arms are mounted with the mobile body and extendable from the mobile body at a position above seats of an aircraft, and is movable over the seats and the UV lamps are directed to the seat surfaces, and when extended from the mobile body and back into mobile body are maintained above the seat level, such that the UV-C lamps are located in a relatively upper portion of the mobile body; and including a hinge between the respective arms and the mobile body, the hinge permitting the upward movement of the arms between an extended position, selectively different horizontal positions, and an upward position essentially being over a body portion of the mobile body.

13. The method of claim 7 wherein the arms are mounted with the mobile body and extendable from the mobile body at a position movable over the seats and the UV-C lamps are directed to the seat surfaces, and when extended from the mobile body and back into mobile body are above the seat level, such that the UV-C lamps are located in an upper portion of the mobile body, and wherein the multiple UV-C lamps are set up in end to end or array relationship.

*14. A method of sanitizing seat surfaces in an area, the area having multiple rows of seats comprising the steps of:*

*a) providing a sanitization device including a mobile body configured to travel through the area;*

*b) extending a portion of the sanitization device from the mobile body across a seat surface, a source of germicidal UV radiation being mounted on the portion of the sanitization device;*

*c) moving the portion of the sanitization device across a first seat surface;*

*d) exposing the first seat surface to germicidal UV radiation produced by the source at a predetermined dosage;*

*e) moving the mobile body through the area while the portion of the sanitization device moves over other seat surfaces of subsequent seat rows; and*

*f) directing the source of germicidal UV radiation to the other seat surfaces at the predetermined dosage while the device moves the portion of the sanitization device over the other seat surfaces; the mobile body being powered by a power source, the mobile body being operated and moved by an operator, the operator being protected by skin and eye protection, providing the UV radiation by UV lamps while the mobile body moves and while the portion extends from the body, and wherein the portion is extendable from the mobile body between different extendible positions and is movable over multiple seats and the UV lamps are directed to the surfaces of the multiple seats, and wherein the UV lamps are movable inwardly towards the device and outwardly from the device, and wherein the portion is extendable from the mobile body by movement from a position with the body to the different positions from the body,*

*g) moving the sanitization device under motorized action to extend at a horizontal angle relative to the mobile body and a surface to be sanitized and to effect sanitization when so extended, the moving of the sanitization device under motorized action being in a track in the mobile body to permit movement in a vertical position upwardly and downwardly;*

*h) operating of the sanitization device to permit a portion of the sanitization device to move under motorized action from the vertical position to the horizontal angle, while being located in the track;*

*i) the operating of the sanitization device to permit a portion of the sanitization device to be movable under*

*motorized action at different angular positions between the vertical position to the horizontal angle while being located in the track, and*

*j) the UV radiation source being operable to direct and effect UV radiation at the surface to be sanitized in the vertical position, horizontal position and different angular positions, and wherein the mobile body includes wheels for permitting travel in a forwards direction, locating a second UV radiation source below the top of the device and adjacent to the wheels to project UV radiation from the second UV radiation source outwardly, sideways and transversely from the mobile body and in adjacency to the floor as the device travels forwardly.*

*15. The method of claim 14 including a remote control for permitting the operator to control the device while remotely located from the device and communicating through the internet with the operator.*

*16. The method of claim 14 wherein the area is a movie theater, theater, sports arena, arena, entertainment arena, or waiting room.*

*17. The method of claim 14 wherein the area is a venue of public assembly, a form of mass transit, a mass transportation vehicle, or a passenger area at the location.*

*18. The method of claim 14 wherein the area is an area of mass transportation, a vehicle, a collection and discharge area, an assembly location relating to buses, trains, ferries and forms of passenger conveyance.*

*19. The method as claimed in claim 14 wherein the sanitization device is movable inwardly and outwardly at different angles under motorized action relative to the mobile body across the surface while effecting the sanitization and wherein the device is operable under motorized action upwardly and downwardly across the surface while effecting the sanitization.*

*20. The method as claimed in claim 14 operable so that the sanitization device can move under motorized action upwardly and downwardly across the surface while directing and effecting the sanitization.*

*21. The method as claimed in claim 14 wherein the UV radiation source is arranged to run relatively vertically under motorized action in a track upwardly or downwardly and an arm is provided to direct the UV radiation source from the track so that the UV radiation source is enabled to adopt different angles relative to the horizontal or vertical relationship.*

*22. The method as claimed in claim 14 wherein the track permits the UV radiation source to move under motorized action inwardly and outwardly in the track relative to the mobile device at a different angle the mobile body, and permitting the UV radiation source to adopt varying angular positions under motorized action relative to the track, including switching an actuator to move under motorized action a wing assembly, being a frame and a wing, in the track upwardly and downwardly vertically, and operating the actuator to permit the wing to move under motorized action from the vertical position to the horizontal position and to selected angular positions between the vertical position and horizontal position, while the frame remains in the vertical position.*

*23. The method as claimed in claim 14 further comprising a step of sanitizing a floor surface; the device being operable under motorized action upwardly and downwardly across the floor surface while effecting the sanitization, a wing movably directed downwardly under motorized action to clean the floor, and in the horizontal angle the wing being disposable horizontally, and a sensor for establishing a degree of adjacency to the floor to provide for effective and efficient use.*

*24. The method as claimed in claim 14 wherein the UV source is directed upwardly and downwardly at the same time.*

*25. A method of sanitizing surfaces in an area, comprising the steps of: a) providing a sanitization device including a mobile body configured to move through the area; b) locating a portion of the sanitization device in adjacency to a surface to be sanitized, a source of germicidal UV radiation being mounted on the portion of the sanitization device; c) moving the portion of the sanitization device relative to a surface to be sanitized; d) exposing the surface to germicidal UV radiation produced by the source at a predetermined dosage; e) moving the mobile body through the area while the portion of the sanitization device moves over other surfaces; and f) directing the source of germicidal UV radiation to the other surfaces at the predetermined dosage while the device moves the portion of the sanitization device over the other surfaces; the mobile body being powered by a power source, the mobile body being operated and driven by an operator, the operator being protected by skin and eye protection, providing the UV radiation by UV lamps while the mobile body moves, and wherein the UV lamps are directed to the surfaces; g) the moving and locating the sanitization device being under motorized action to extend at a horizontal angle relative to the mobile body and a surface to be sanitized and to effect sanitization when so extended, h) the moving of the sanitization device under motorized action being in a track in the mobile body to permit movement in a vertical position upwardly and downwardly; i) operating of the sanitization device being to permit a portion of the-sanitization device to move under motorized action from the vertical position to the horizontal angle, while being located in the track; j) the operating of the sanitization device being to permit a portion of the sanitization device to be movable under motorized action at different angular positions between the vertical position to the horizontal angle while being located in the track, and k) the UV radiation source being operable to direct and effect UV radiation at the surface to be sanitized in the vertical position, horizontal position and different angular positions, and wherein the mobile body includes wheels for permitting travel in a forwards direction, locating a second UV radiation source below the top of the device and adjacent to the wheels to project UV radiation from the second UV radiation source outwardly, sideways and transversely from the mobile body and in adjacency to the floor as the device travels forwardly.*

*26. The method of claim 25 including an arm extendable from the device as it moves about an area, and including the step of extending the arm from the device to a position remote from the device and adjacent the surface to be sanitized.*

*27. The method of claim 25 wherein the area is a movie theater, theater, sports arena, arena, entertainment arena, or waiting room.*

*28. The method of claim 25 wherein the area is a venue of public assembly, a form of mass transit, a mass transportation vehicle, or a passenger area at the location.*

*29. The method of claim 25 wherein the area is an area of mass transportation, selectively a vehicle, a collection and discharge area, an assembly location relating to buses, trains, ferries and forms of passenger conveyance.*

*30. The method as claimed in claim 25 wherein the sanitization device is movable inwardly and outwardly at*

*different angles under motorized action relative to the mobile body across the surface while effecting the sanitization and wherein the device is operable under motorized action upwardly and downwardly across the surface while effecting the sanitization.*

*31. The method as claimed in claim 25 operable so that the sanitization device can move under motorized action upwardly and downwardly across the surface while directing and effecting the sanitization.*

*32. The method as claimed in claim 25 wherein the UV radiation source is arranged to run relatively vertically under motorized action in a track upwardly or downwardly and an arm is provided to direct the UV radiation source from the track so that the UV radiation source is enabled to adopt different angles relative to the horizontal or vertical relationship.*

*33. The method as claimed in claim 25 wherein the track permits the UV radiation source to move under motorized action inwardly and outwardly in the track relative to the mobile device at a different angle the mobile body, and permitting the UV radiation source to adopt varying angular positions under motorized action relative to the track, including switching an actuator to move under motorized action a wing assembly, being a frame and a wing, in the track upwardly and downwardly vertically, and operating the actuator to permit the wing to move under motorized action from the vertical position to the horizontal position and to selected angular positions between the vertical position and horizontal position, while the frame remains in the vertical position.*

*34. The method as claimed in claim 25 for sanitizing a floor surface; the device being selectively operable under motorized action upwardly and downwardly across the floor surface while effecting the sanitization, a wing movably directed downwardly under motorized action to clean the floor, and in the horizontal angle the wing being disposable horizontally, and a sensor for establishing a degree of adjacency to the floor to provide for effective and efficient use.*

*35. The method as claimed in claim 25 wherein the UV source is directed upwardly and downwardly at the same time.*

*36. The method as claimed in claim 25 wherein the second UV radiation source is mounted on the mobile body to be located essentially within the perimeter of the mobile body.*

*37. The method as claimed in claim 25 wherein the second UV source is mounted on the mobile body to be non-movable relative to the mobile body.*

* * * * *